US012728104B2

(12) United States Patent
Lisanti et al.

(10) Patent No.: US 12,728,104 B2
(45) Date of Patent: Sep. 8, 2026

(54) THERAPEUTIC METHODS FOR PREVENTING TUMOR METASTASIS AND TUMOR RECURRENCE

(71) Applicant: LUNELLA BIOTECH, INC., Ottawa (CA)

(72) Inventors: Michael P. Lisanti, Didsbury Village (GB); Federica Sotgia, Didsbury Village (GB)

(73) Assignee: LUNELLA BIOTECH, INC., Ontario (CA)

( * ) Notice: Subject to any disclaimer, the term of this patent is extended or adjusted under 35 U.S.C. 154(b) by 754 days.

(21) Appl. No.: 17/921,060

(22) PCT Filed: Apr. 23, 2021

(86) PCT No.: PCT/IB2021/053378

§ 371 (c)(1),
(2) Date: Oct. 24, 2022

(87) PCT Pub. No.: WO2021/214727

PCT Pub. Date: Oct. 28, 2021

(65) Prior Publication Data

US 2023/0172879 A1 Jun. 8, 2023

Related U.S. Application Data

(60) Provisional application No. 63/014,838, filed on Apr. 24, 2020.

(51) Int. Cl.

| | |
|---|---|
| ***A61K 31/137*** | (2006.01) |
| ***A61K 31/122*** | (2006.01) |
| ***A61K 31/167*** | (2006.01) |
| ***A61K 31/36*** | (2006.01) |
| ***A61K 31/40*** | (2006.01) |
| ***A61K 31/4375*** | (2006.01) |
| ***A61K 31/438*** | (2006.01) |
| ***A61K 31/44*** | (2006.01) |
| ***A61K 31/4439*** | (2006.01) |
| ***A61K 31/4706*** | (2006.01) |
| ***A61K 31/4745*** | (2006.01) |
| ***A61K 31/519*** | (2006.01) |
| ***A61K 31/55*** | (2006.01) |

(Continued)

(52) U.S. Cl.

CPC .......... *A61K 31/137* (2013.01); *A61K 31/122* (2013.01); *A61K 31/167* (2013.01); *A61K 31/36* (2013.01); *A61K 31/40* (2013.01); *A61K 31/4375* (2013.01); *A61K 31/438* (2013.01); *A61K 31/44* (2013.01); *A61K 31/4439* (2013.01); *A61K 31/4706* (2013.01); *A61K 31/4745* (2013.01); *A61K 31/519* (2013.01); *A61K 31/55* (2013.01); *A61K 31/551* (2013.01); *A61K 31/65* (2013.01); *A61K 31/7048* (2013.01); *A61K 31/7052* (2013.01); *A61P 35/04* (2018.01)

(58) Field of Classification Search

CPC .. A61K 31/137; A61K 31/122; A61K 31/167; A61K 31/36; A61K 31/40; A61K 31/4375; A61K 31/438; A61K 31/44; A61K 31/4439; A61K 31/4706; A61K 31/4745; A61K 31/519; A61K 31/55; A61K 31/551; A61K 31/65; A61K 31/7048; A61K 31/7052; A61P 35/04

USPC ........................................................... 514/29

See application file for complete search history.

(56) References Cited

FOREIGN PATENT DOCUMENTS

| | | | |
|---|---|---|---|
| WO | WO 2018/195434 | * | 10/2018 |
| WO | 2018/213764 | | 11/2018 |

(Continued)

OTHER PUBLICATIONS

Glossary of Medical Education Terms, Institute for International Medical Education (IIME), https://www.iime.org/glossary.htm#P ( accessed on Apr. 20, 2024) (Year: 2024).*

(Continued)

*Primary Examiner* — Yih-Horng Shiao
(74) *Attorney, Agent, or Firm* — Nixon & Vanderhye, P.C.

(57) ABSTRACT

Cancer stem cells are responsible for tumor recurrence, distant metastasis and drug-resistance, in the vast majority of cancer patients. There exists an urgent need to identify new mitochondrial inhibitor drugs that can target and eradicate CSCs, and companion diagnostics to identify candidates for mitochondrial inhibition therapy. In 3D mammospheres, 25 mitochondrial-related proteins were over 100-fold over-expressed in a large collection of transcriptional profiling data from ER(+) breast cancer patients. These 25 proteins may be used to derive short gene signatures to predict the likelihood of distant metastasis and tumor recurrence. For example, the 4-gene signature of ACLY, VDAC3, HADH2, and COX6B1 may be used for predicting the likelihood of distant metastasis, with a hazard ratio of 1.91-fold (P=2.2e−08). A pharmaceutically effective amount of a mitochondrial inhibitor may be administered to a candidate having elevated expression of the genes in a gene signature. Five example mitochondrial inhibitors showed preferential and selective inhibition of tumor cell metastasis, without causing significant toxicity. Mechanistically, all five mitochondrial inhibitors have been previously shown to induce ATP-depletion in cancer cells. Gene signatures composed of 6-9 large mitochondrial ribosomal proteins also show prognostic value in predicting distant metastasis, tumor recurrence, and Tamoxifen resistance, in both ER(+) and ER(−) breast cancer patients. The disclosed gene signatures may be used as companion diagnostics to assess which patients may benefit most from mitochondrial inhibition therapy.

6 Claims, 12 Drawing Sheets

(51) Int. Cl.

| | |
|---|---|
| ***A61K 31/551*** | (2006.01) |
| ***A61K 31/65*** | (2006.01) |
| ***A61K 31/7048*** | (2006.01) |
| ***A61K 31/7052*** | (2006.01) |
| ***A61P 35/04*** | (2006.01) |

(56) References Cited

FOREIGN PATENT DOCUMENTS

WO WO 2019/075209 A1 4/2019
WO WO 2019/246173 A1 12/2019

OTHER PUBLICATIONS

International Search Report and Written Opinion of the ISA for PCT/IB2021/053378 dated Jul. 7, 2021, 16 pages.

Lamb et al., Mitochondria as new therapeutic targets for eradicating cancer stem cells: Quantitave proteomics and functional validation via MCT1/2 inhibition. Oncotarget, Nov. 15, 2014, vol. 5, No. 22, pp. 11029-11037. (to follow).

Sotgia et al., A mitochondrial based oncology platform for targeting cancer stem cells (CSCs): MITO-ONC-RX. Cell Cycle, Sep. 26, 2018, vol. 17, No. 17, pp. 2091-2100. (to follow).

DeLuca et al. Mitochondrial biogenesis is required for the anchorage independent survival and propagation of stem-like cancer cells., Oncotarget, Jun. 9, 2015, vol. 6, No. 17, pp. 14777-14795. (to follow).

Sotgia et al., Mitochondrial markers predict recurrence, metastasis and amoxifen-resistance in breast cancer patients: Early detection of treatment failure with companion diagnostics. Oncotarget, Jul. 27, 2017, vol. 8, No. 40, pp. 68730-68745. (to follow).

Bela Ozsvari et al., "Mitoriboscins: Mitochondrial-based Therapeutics Targeting Cancer Stem Cells (CSCs), Bacteria and Pathogenic Yeast", Oncotarget, vol. 8, No. 40, Sep. 15, 2017, pp. 67457-67472, XP055546993.

* cited by examiner

Large-Mito-Ribosome-Genes

ER(-)/Basal Sub-type

Overall Survival
(6 Gene Signature)

THERAPEUTIC METHODS FOR PREVENTING TUMOR METASTASIS AND TUMOR RECURRENCE

CROSS-REFERENCE TO RELATED APPLICATIONS

This application is the U.S. national phase of International Application No. PCT/IB2021/053378 filed Apr. 23, 2021 which designated the U.S. and claims priority to U.S. 63/014,838 filed Apr. 24, 2020, the entire contents of each of which are hereby incorporated by reference.

FIELD

The present disclosure relates to pharmaceutical compounds and companion diagnostics for treating and preventing cancer metastasis, recurrence, and Tamoxifen resistance, in breast cancer.

BACKGROUND

Breast cancer treatment requires a multi-disciplinary approach, involving an extensive medical team consisting of specialized surgeons, medical oncologists, oncology nurses, as well as radiologists and radiology technicians, to perform anti-cancer therapy, which consists of tumor excision, chemo- or hormonal-therapy, as well as radiation therapy. Despite these major advances, many patients still ultimately undergo treatment failure, in the form of tumor recurrence and distant metastasis. Unfortunately, distant metastasis causes premature death, in over 90% of cancer patients with treatment failure. Therefore, there is a clear need to develop new strategies to prevent cancer metastasis.

Local and distant metastases are thought to be caused by a small sub-population of cancer cells, known as cancer stem cells (CSCs). These CSCs are unique, in the sense that they can regenerate tumors in immune-deficient mice, as xenografts, and they undergo anchorage-independent proliferation and the EMT, allowing them to disseminate throughout the body, thereby creating local and distant metastatic lesions, which are largely chemo- and radio-therapy resistant. However, it remains largely unknown, what are the precise vulnerabilities of CSCs.

Recently, the inventors identified cancer cell mitochondria as a new promising therapeutic target for the eradication of CSCs. New evidence suggests that CSCs have elevated levels of mitochondrial biogenesis that helps to energetically drive their rapid propagation and anchorage-independent growth. In support of this notion, metastatic breast cancer cells in positive lymph nodes, removed from patients, show a significant increase in mitochondrial Complex IV activity, as seen by histochemical- and immuno-staining.

Mitochondrial biogenesis is strictly dependent on the function of the mitochondrial ribosome, which consists of both large and small subunits, to effectively carry out the mitochondrial protein translation of 13 key genes that are absolutely required for OXPHOS and mitochondrial ATP production. In eukaryotic cells, mitochondria originally evolved from engulfed aerobic bacteria, an event estimated to have occurred approximately 1.5 billion years ago. Because of this evolutionary relationship, certain FDA-approved drugs inhibit mitochondrial protein translation as an off-target side effect. For example, Doxycycline (a Tetracycline family member) negatively affects the small mitochondrial ribosome, while Azithromycin (an Erythromycin family member) inhibits the large mitochondrial ribosome. Inhibiting mitochondrial protein translation has been demonstrated as an effective approach for inhibiting CSC propagation in a wide variety of cancer types. Both Doxycycline and Azithromycin effectively inhibit the anchorage-independent propagation of CSCs, as assessed using the 3D-tumorsphere assay, in cell lines derived from 8 different cancer types, including breast cancers (MCF7, T47D, MDA-MB-231 and MCF10.DCIS.COM).

In prior work, the inventors demonstrated that mitochondrial biogenesis inhibitors successfully inhibited tumorsphere formation in a wide-variety of cell lines from several tumor types. Table 1, below, lists cancer cell lines that the inventors' prior work has demonstrated to be susceptible to mitochondrial biogenesis inhibitors. Given these results, the present approach is effective for numerous cancer types.

TABLE 1

Mitochondrial biogenesis inhibitors are effective against a wide variety of cancer types.

| Cancer Type | Cell Line(s) |
|---|---|
| Breast (ER+) | MCF7 |
| | T47D |
| Breast (ER−) | MDA-MB-231 |
| DCIS | MCF10.DCIS.com ("pre-malignant") |
| Ovarian | SKOV3 |
| | Tov21G |
| | ES2 |
| Prostate | PC3 |
| Pancreatic | MIA PaCa2 |
| Lung | A549 |
| Melanoma | A375 |
| Glioblastoma | U-87 MG |

In view of these data, the inventors proposed that these off-target side-effects could be clinically "re-purposed" as a therapeutic effect. A recent Phase II clinical trial also showed that Doxycycline treatment (200-mg/day for 2-weeks) of early stage breast cancer patients reduced their CSC tumor load (as assessed by CD44 immuno-staining), between about 17% and 67%, with a positive response rate approaching nearly 90%. Therefore, inhibition of mitochondrial protein translation may be a new valuable target for eradicating CSCs in patients.

SUMMARY

Cancer stem cells, or CSCs, have been proposed to be responsible for tumor recurrence, distant metastasis and drug-resistance, in the vast majority of cancer patients. Therefore, there is an urgent need to identify new drugs that can target and eradicate CSCs. To identify new molecular targets that are unique to CSCs, the inventors previously compared MCF7 2D-monolayers with 3D-mammospheres, which are enriched in CSCs. The inventors observed that 25 mitochondrial-related proteins were >100-fold over-expressed in 3D-mammospheres in a large collection of transcriptional profiling data from ER(+) breast cancer patients. These 25 proteins may be used to derive short gene signatures to predict the likelihood of distant metastasis and tumor recurrence. In one embodiment, a 4-gene signature may be used for predicting distant metastasis in breast cancer patients. The 4-gene signature had a hazard ratio of 1.91-fold (P=2.2e−08) using the transcriptional profiling data. The result provides clinical evidence to support a role for CSC mitochondria in metastatic dissemination.

The present approach provides gene signatures and uses thereof as a diagnostic or prognostic platform for use in conjunction with cancer treatments and therapies, to identify candidates for mitochondrial inhibitor therapy. In the present approach, measuring the levels of expression of the genes may involve measuring the level of expression of mRNA. In some embodiments, measuring the levels of expression of the genes involves measuring the levels of expression of the proteins encoded by the genes. In some embodiments, gene expression levels may be measured as increased expression levels of the genes relative to a control. The gene signatures described herein may be used to identify candidates for mitochondrial inhibition therapy. As described herein, a series of mitochondrial inhibitors, previously shown to target mitochondria and selectively inhibit 3D-mammosphere formation in MCF7 cells and cell migration in MDA-MB-231 cells, were demonstrated to prevent and inhibit metastasis and recurrence. The five demonstrative mitochondrial inhibitors evaluated showed preferential and selective inhibition of tumor cell metastasis, without causing significant toxicity. Mechanistically, all five of the demonstrative mitochondrial inhibitors have been previously shown to induce ATP-depletion in cancer cells. It should be appreciated that other mitochondrial inhibitors may be used for mitochondrial inhibition therapy, without departing from the present approach.

Because 3 of these 5 inhibitors were designed to target the large mitochondrial ribosome, the inventors also demonstrated that genes encoding the large mitochondrial ribosomal proteins (MRPL) show prognostic value in the prediction of distant metastasis in both ER(+) and ER(−) breast cancer patients. For example, gene signatures composed of 6 to 9 MRPL mRNA-transcripts were indeed sufficient to predict distant metastasis, tumor recurrence and Tamoxifen resistance. These gene signatures may be used as companion diagnostics to identify cancer patients that may benefit from mitochondrial inhibition therapy. Once identified, candidates may receive a pharmaceutically effective amount of a mitochondrial inhibitor, such as the Mitoriboscin compounds, Bis-TPP, and Dodecyl-TPP discussed herein. It should be appreciated that this disclosure provides the necessary proof-of-concept, and in vivo functional evidence, that mitochondrial inhibitors can successfully and selectively target the biological process of cancer metastasis and recurrence.

Embodiments of the present approach may take the form of methods for preventing and/or reducing the likelihood of tumor metastasis and tumor recurrence in a patient. A biological sample of a cancer from the patient may be obtained, and the expression level of genes in one or more gene signatures may be determined. For example, the level of at least one mitochondrial biomarker in the biological sample of a CSC-based mitochondrial-related gene signature comprising ACLY, VDAC3, HADH2, COX6B1, ATP5B, MCCC1, SLC25A10, TIMM8A, ECH1, ACACA, HSPA9, CHCHD2, and CCDC47. The determined levels may be compared to a control or threshold level for the biomarkers. If the determined level exceeds the threshold level, then the patient providing the biological sample may be identified as a candidate for mitochondrial inhibitor therapy, and may be administered a pharmaceutically effective amount of at least one mitochondrial biogenesis inhibitor.

In some embodiments, the level of each gene in a gene signature may be evaluated. For example, each biomarker in the CSC-based mitochondrial-related gene signature of ACLY, VDAC3, HADH2, COX6B1, ATP5B, MCCC1, SLC25A10, TIMM8A, ECH1, ACACA, HSPA9, CHCHD2, and CCDC47, may be determined. In some embodiments, the CSC-based mitochondrial-related gene signature comprises each of ACLY, VDAC3, HADH2, and COX6B1. In some embodiments, the gene signature may be comprised of large mitochondrial ribosomal proteins (MRPL). For example, the gene signature may comprise one or more, or each, of MRPL15, MRPL13, MRPL17, MRPL46, MRPL18, MRPL48, MRPL3, MRPL24, and MRPL4. In some embodiments, the patient and potential candidate may be a patient receiving hormone therapy, and the gene signature may include each of MRPL15, MRPL46, MRPL17, MRPL24, MRPL18, and MRPL13. In some embodiments, the patient and potential candidate may be a patient receiving hormone therapy, and the gene signature may include each of MRPL15, MRPL3, MRPL17, MRPL18, MRPL24, MRPL13, MRPL48, and MRPL46. In some embodiments, the large mitochondrial ribosome-related gene signature may include one or more, or each of, MRPL42, MRPL41, MRPL54, MRPL13, MRPL36, and MRPL22.

In some embodiments, the present approach may take the form of a kit having the reagents for detecting expression levels of the genes in one or more of the gene signatures described herein. For example, the kit may have nucleic acid probes that specifically bind to nucleotide sequences corresponding to the genes in one or more of the gene signatures described, and a means of labelling the nucleic acids. As another example, the kit may have antibodies or ligands that specifically bind to polypeptides encoded by the genes in one or more of the gene signatures described herein, and a means of labelling the antibodies or ligands that specifically bind to polypeptides or peptides encoded by the genes.

In embodiments of the present approach, a patient whose gene expression levels are elevated relative to a control or a threshold value may be classified as a candidate for mitochondrial inhibitor therapy, and administered a pharmaceutically effective amount of a mitochondrial inhibitor. Examples of mitochondrial inhibitors include tetracycline, doxycycline, tigecycline, minocycline, eyrthromycin, azithromycin, clarithromycin, pyrvinium pamoate, atovaquone, bedaquiline, irinotecan, sorafenib, niclosamide, berberine, stiripentol, chloroquine, etomoxir, perhexiline, a mitoriboscin, a mitoketoscin, a mitoflavoscin, a mitoflavin, a TPP-derivative, an mDIVII-1 derivative, caffeic acid phenyl ester, an antimitoscin, and a repurposcin. Specific Mitoriboscin compounds and TPP-derivative compounds, including Bis-TPP and Dodecyl-TPP, are discussed below. It should be appreciated that other mitochondrial inhibitors may be effective.

Embodiments of the present approach may be recognized by those having ordinary skill in the art, having reviewed the following detailed description.

DRAWINGS

DETAILED DESCRIPTION

Figure 1:
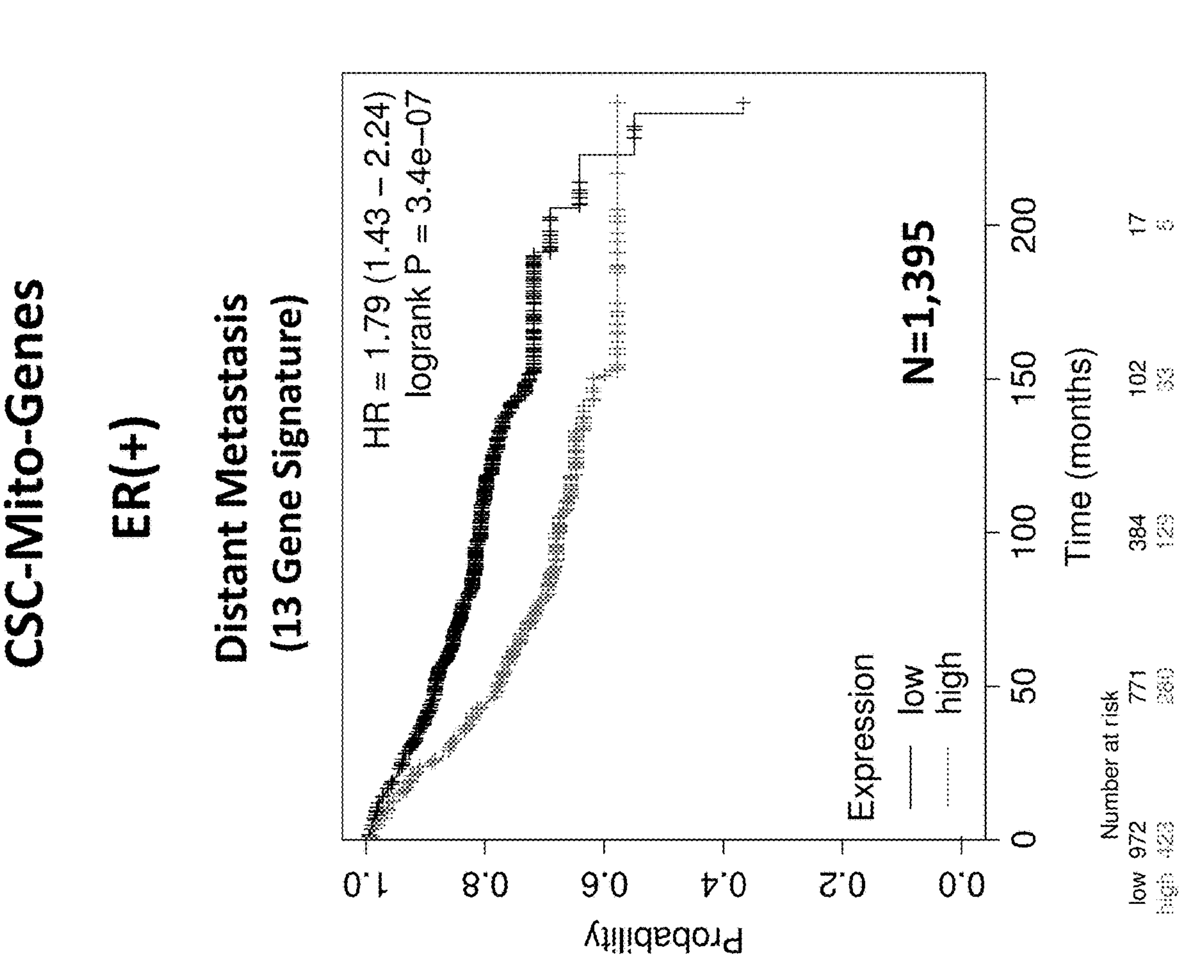
FIG. 1 shows a Kaplan-Meier curve for the CSC-based mitochondrial 13-gene signature.

The following description includes the currently contemplated modes of carrying out exemplary embodiments of the present approach. The following description is not to be taken in a limiting sense, and is made merely for the purpose of illustrating the general principles of the invention.

The term "salt" of a compound relates to corresponding salt prepared by using acid selected from the group of mineral acids, such as hydrochloric acid, hydrobromic acid, phosphoric acid, metaphosphoric acid, nitric acid and sulphuric acid, and organic acids, such as tartaric acid, acetic acid, trifluoroacetic acid, citric acid, malic acid, lactic acid, fumaric acid, benzoic acid, glycolic acid, gluconic acid and succinic acid, and alkylsulphonic acids such as methanesulphonic, ethanesulphonic acids, ethane-1,2-disulfonic acid and 2-hydroxyethanesulfonic acid and arylsulphonic acids such as benzene sulfonic acid, 2-naphthalenesulfonic acid, p-toluenesulphonic acid and naphthalene-1,5-disulfonic acid.

The phrase, "pharmaceutically effective amount" as used herein indicates an amount necessary to administer to a host, or to a cell, tissue, or organ of a host, to achieve a therapeutic result, such as the regulating, modulating, or inhibiting protein kinase activity, e.g., inhibition of the activity of a protein kinase, or treatment of cancer. It should be appreciated that the person having an ordinary level of skill in the art can use known methods to determine the pharmaceutically effective amount for a given compound and a candidate in need of treatment. For example, a physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. For example, common and known methods in the art may be used to establish both the maximum tolerable dose of a compound, and the effective dose that provides a detectable therapeutic benefit to a person in need thereof. Likewise, common and known methods in the art may be used to determine the dosage and dosing schedule for administering the therapeutic agent sufficient to provide a detectable therapeutic benefit. The demonstrative dosing examples disclosed herein in no way limit the potential dosage and dosing schedules that may be provided under the present approach.

The term "about" means having a value falling within an accepted standard of error of the mean, when considered by one of ordinary skill in the art. As would be expected, the meaning of "about" depends on the context in which it is used. Frequently, the term "about" may refer to ±5%, and preferably ±2.5%, and more preferably +1% of the value or range to which it refers. For example, in the context of weight fractions, the phrase "about 20%" may mean 20%±5%, preferably 20%±2.5%, and more preferably 20%±1%. In the absence of specific reference, the term "about" denotes ±5% of the stated value.

The terms "treat," "treated," "treating," and "treatment" include the diminishment or alleviation of at least one symptom associated or caused by the state, disorder or disease being treated, in particular, cancer. In certain embodiments, the treatment comprises diminishing and/or alleviating at least one symptom associated with or caused by the cancer being treated, by the compound of the invention. For example, treatment can be diminishment of one or several symptoms of a cancer or complete eradication of a cancer.

The term "control" typically refers to a sample, reference, or standard that is used as a basis for comparison with one or more experimental or test samples. An experimental sample can be a tumor specimen or sample obtained from a patient. The control may be, for example, a sample that is obtained from a healthy individual free of cancer or tumors. As another example, the control may be a non-tumor tissue sample taken from the individual having the cancer or tumor, such as healthy breast tissue. The control may also be a standard reference value, or a range of values, or a historical control. By way of example, a standard range of values may be obtained from a previously tested control sample, e.g., a group of samples that represent baseline or normal values, such as the levels of the genes of non-tumor breast tissue; or a previously-tested group of individuals who experienced cancer recurrence or metastasis, or did not experience cancer recurrence or metastasis. In addition, controls that can serve as standards of comparison to a test sample for the determination of differential gene expression include samples that are believed to be normal, such as from a subject who does not have a cancer or tumor. A range of values, such as laboratory values or values obtained from in vitro experiments, may also be used as a control. In addition and without limitation, a control can be a relative amount of gene expression in a biological sample, or test population.

Contemporary thinking indicates that CSCs are the etiological cause of treatment failure in most cancer patients, as they are the cellular drivers of tumor recurrence, metastasis and drug-resistance. As a consequence, new therapeutic approaches are needed to effectively eliminate CSCs. The inventors' previous studies identified CSC mitochondria as a potential new therapeutic target. More specifically, the inventors experimentally observed that MCF7-derived 3D-mammospheres are specifically enriched in mitochondrial proteins; 25 mitochondrial proteins showed greater than 100-fold over-expression, while 9 of these proteins were infinitely up-regulated, as compared with 2D-monolayers. As disclosed herein, these proteomic data were used to generate short mitochondrial gene signatures that could be employed as prognostic tools to predict distant metastasis (in N=1,395 patients) and tumor recurrence (in N=3,082 patients), in a large collection of ER(+) breast cancer patients. For example, described below is a 4-gene signature of ACLY, VDAC3, HADH2, and COX6B1 for predicting distant metastasis, resulting in a hazard ratio of 1.91-fold (P=2.2e−08). This clinical evidence supports the understanding that CSC mitochondria may play a critical functional role in the metastatic dissemination of cancer cells.

To further evaluate this understanding, the inventors used a well-established animal model, the chorio-allantoic membrane (CAM) in chicken eggs, to test a series of mitochondrial inhibitors. These mitochondrial inhibitors, including the Mitoriboscins, have been previously described to effectively inhibit 3D-mammosphere formation in MCF7 cells and cell migration in MDA-MB-231 cells. All five of these mitochondrial inhibitors selectively prevented MDA-MB-231 tumor metastasis, but had only minor effects or no effect on tumor formation. These studies also provide the necessary in vivo functional evidence, that mitochondrial inhibitors can successfully prevent cancer metastasis. These findings could have important clinical implications, for ultimately preventing treatment failure in breast cancer patients.

Since the Mitoriboscins were originally engineered to inhibit the large mitochondrial ribosome, the inventors also focused on whether the large mitochondrial ribosomal gene transcripts have any prognostic value, for predicting distant metastasis in ER(+) breast cancer patients. Importantly, signatures containing MRPL gene transcripts were effective in predicting metastasis, recurrence and Tamoxifen-resistance. Similar results were also obtained in ER(−) breast cancer patients. As a consequence of the success of this approach, these large mito-ribosome gene signatures may ultimately be useful as new companion diagnostics, to guide decisions to determine which patients would benefit from anti-mito-ribosome therapy.

To design novel therapeutics to more effectively target the mitochondria, the inventors used the known 3D-structure of the large mammalian mitochondrial ribosome to perform in Silico library screening coupled with phenotypic drug screening. This process allowed the inventors to isolate a family of new compounds, called Mitoriboscins. Compounds in the Mitoriboscin family inhibit mitochondrial oxygen consumption rates, resulting in cellular ATP-depletion and potent inhibition of 3D-mammosphere formation, all with an IC-50 in the low micro-molar range. Certain compounds in this family have been described in International Application Publication WO 2018/0170109A1, filed Mar. 14, 2018 and incorporated by reference in its entirety.

Demonstrative Mitoriboscin compounds are shown below, as structures a) through j). For the avoidance of doubt, compounds a) through j) are shown below and are referred to as 23/E9, 23/G4, 24/B10, 24/D2, 24/F9, 24/H6, 24/H9, 5/B3, 25/E3, and 26/H4, respectively, in the incorporated application.

a)

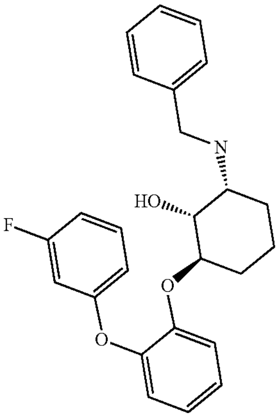

, b)

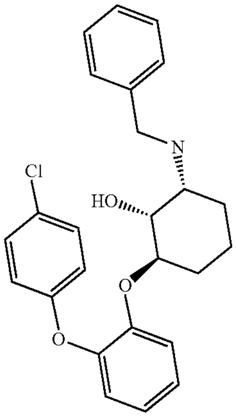

, c)

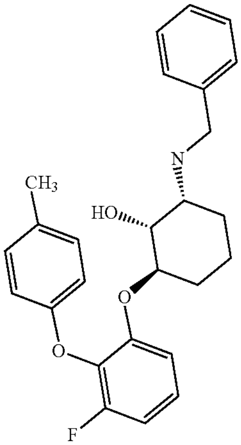

, d)

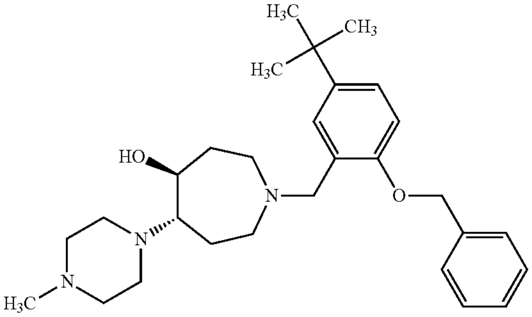

,

-continued e)

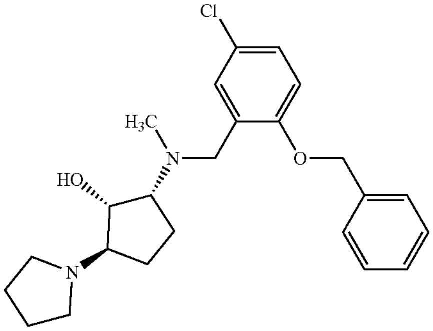

, f)

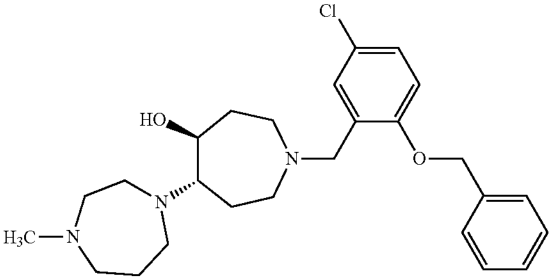

, g)

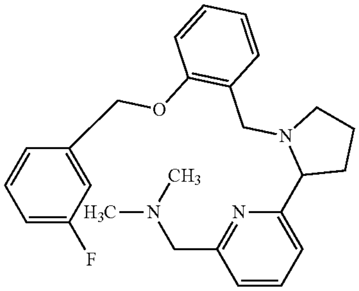

, h)

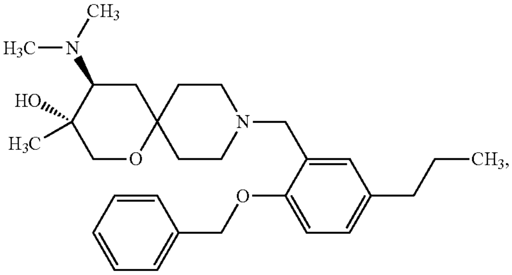

, i)

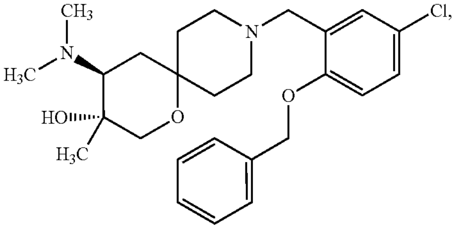

and

-continued j)

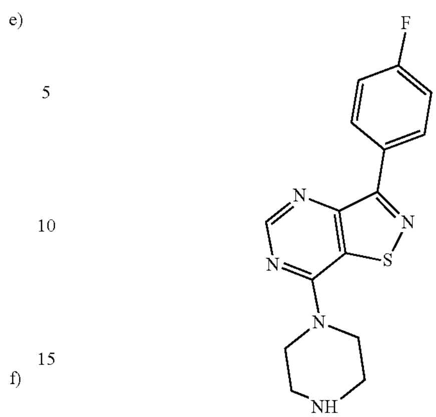

.

Further evaluation of selected Mitoriboscin compounds showed minor effects on initial tumor growth, but a functional prevention of cancer metastasis. For example, data described herein shows that Mitoriboscin compound 23/G4 had a minor effects on tumor growth, while Mitoriboscin compounds 24/D4 and 24/F9 had no inhibitory effects on tumor growth. However, all three of these compounds functionally prevented cancer metastasis. Quantitatively similar results were obtained with another independent class of mitochondrial inhibitors, referred to as TPP-Derivatives and described in International Application Publication WO 2019/104115 A1, filed Nov. 21, 2018 and incorporated by reference in its entirety. For example, TPP-Derivative compounds butene-1,4-bis-triphenyl-phosphonium (Bis-TPP) and dodecyl-triphenyl-phosphonium (Dodecyl-TPP) showed functional prevention of cancer metastasis. Bis-TPP and Dodecyl-TPP both contain a TPP moiety, which functions as a chemical signal for mitochondrial targeting. These data provide in vivo functional evidence that five mitochondrial inhibitors can successfully and preferentially target the biological process of cancer cell metastasis, without significant toxicity. International Application Publication WO 2021/024208 A1 described various TPP-Derivative compounds having an improved selectivity for targeting bulk cancer stem cells and preventing or reducing the likelihood of tumor recurrence and/or metastasis, and is incorporated by reference in its entirety. International Application No. PCT/US2020/028414, filed Apr. 16, 2020, describes alkyl-TPP compounds, such as dodecyl-TPP, and is incorporated herein by reference. Although the following description utilizes only a portion of these mitochondrial inhibitor compounds, it should be appreciated that the compounds disclosed in the incorporated references may be used without departing from the present approach. Further, it should be appreciated that other mitochondrial inhibitors may be useful in a mitochondrial inhibition therapy as described below. Additional compounds are under evaluation.

After a breast cancer diagnosis, most patients undergo surgical resection of the primary tumor and are then subsequently treated with hormone-, chemo- and/or radio-therapy, depending on the breast cancer subtype. However, many patients ultimately experience treatment failure, resulting in tumor recurrence and distant metastasis. Unfortunately, distant metastasis is responsible for the premature deaths in the vast majority of cancer patients, approaching over 90%. Therefore, new diagnostics and therapeutics are urgently needed to prevent and treat metastatic disease, which has been attributed to the existence and resurgence of a small sub-population of cancer cells, known as cancer stem cells or CSCs.

In order to identify new molecular targets that are selectively up-regulated in CSCs, the inventors previously carried out unbiased proteomics analysis on MCF7 cell 2D-monolayers, directly compared with MCF7 3D-mammospheres, as mammospheres are known to be highly enriched in CSCs and progenitor cells. As a consequence, the inventors observed that 25 mitochondrial proteins were highly up-regulated by over 100-fold, specifically in 3D-mammospheres.

As described herein, the inventors interrogated whether the mRNA transcripts of these mitochondrial proteins show any prognostic value in large numbers of ER(+) human breast cancer patients. Of the 25 gene transcripts, 13 gene transcripts showed prognostic value in predicting distant metastasis. These genes are ACLY, VDAC3, HADH2, COX6B1, ATP5B, MCCC1, SLC25A10, TIMM8A, ECH1, ACACA, HSPA9, CHCHD2, and CCDC47. The 13 gene transcripts to create a mitochondrial-related gene signature, that effectively predicted distant metastasis in 1,395 patients (HR=1.79; P=3.4e−07). The data, showing the prognostic value of mitochondrial-related proteins up-regulated in MCF7 mammospheres, evaluated in ER(+) breast cancer patients (DMFS/ER(+), N=1,395, >240-months), is shown below in Table 2, below.

TABLE 2

Prognostic value of mitochondrial-related proteins up-regulated in MCF7 mammospheres.

| Probe | Symbol | HR (DMFS) | Log-Rank Test |
|---|---|---|---|
| 201128_s_at | ACLY | 1.72 | 3.1e−05 |
| 208845_at | VDAC3 | 1.66 | 1.2e−05 |
| 202282_at | HADH2 | 1.58 | 7.2e−05 |
| 201441_at | COX6B1 | 1.53 | 0.00017 |
| 201322_at | ATP5B | 1.43 | 0.0016 |
| 218440_at | MCCC1 | 1.40 | 0.0054 |
| 218275_at | SLC25A10 | 1.37 | 0.0048 |
| 205217_at | TIMM8A | 1.37 | 0.0072 |
| 200789_at | ECH1 | 1.35 | 0.0092 |
| 212186_at | ACACA | 1.34 | 0.031 |
| 200690_at | HSPA9 | 1.29 | 0.046 |
| 217720_at | CHCHD2 | 1.28 | 0.028 |
| 217814_at | CCDC47 | 1.28 | 0.032 |
| Combined | | 1.79 | 3.4e−07 |

FIG. 1 shows a Kaplan-Meier curve for the CSC-based mitochondrial 13-gene signature. As can be seen, the 13-gene signature predicts distant metastasis in ER(+) breast cancer patients. The inventors used 13 gene transcripts to create a CSC-based mitochondrial-related gene signature, that effectively predicted distant metastasis in N=1,395 patients (HR=1.79; P=3.4e−07).

To optimize the predictive value of the CSC-based mitochondrial gene signature, the inventors selected the top 4 gene transcripts, having the largest hazard ratios, to construct a short 4-gene signature, which revealed an increase in prognostic value, related to distant metastasis (HR=1.91; P=2.2e−08). Remarkably, this 4-gene signature was also able to predict tumor recurrence in the same patient population (HR=1.68; P=1.2e−15). Table 3, below, shows the prognostic value of mitochondrial-related proteins up-regulated in MCF7 Mammospheres, Evaluated in ER(+) Breast Cancer Patients (DMFS/ER(+)/N=1,395/>240-months).

TABLE 3

Prognostic Value of Mitochondrial-Related Proteins Up-regulated in MCF7 Mammospheres.

| Probe | Symbol | HR (DMFS) | Log-Rank Test |
|---|---|---|---|
| 201128_s_at | ACLY | 1.72 | 3.1e−05 |
| 208845_at | VDAC3 | 1.66 | 1.2e−05 |
| 202282_at | HADH2 | 1.58 | 7.2e−05 |
| 201441_at | COX6B1 | 1.53 | 0.00017 |
| Combined | | 1.91 | 2.2e−08 |

Figures 2A, 2B:
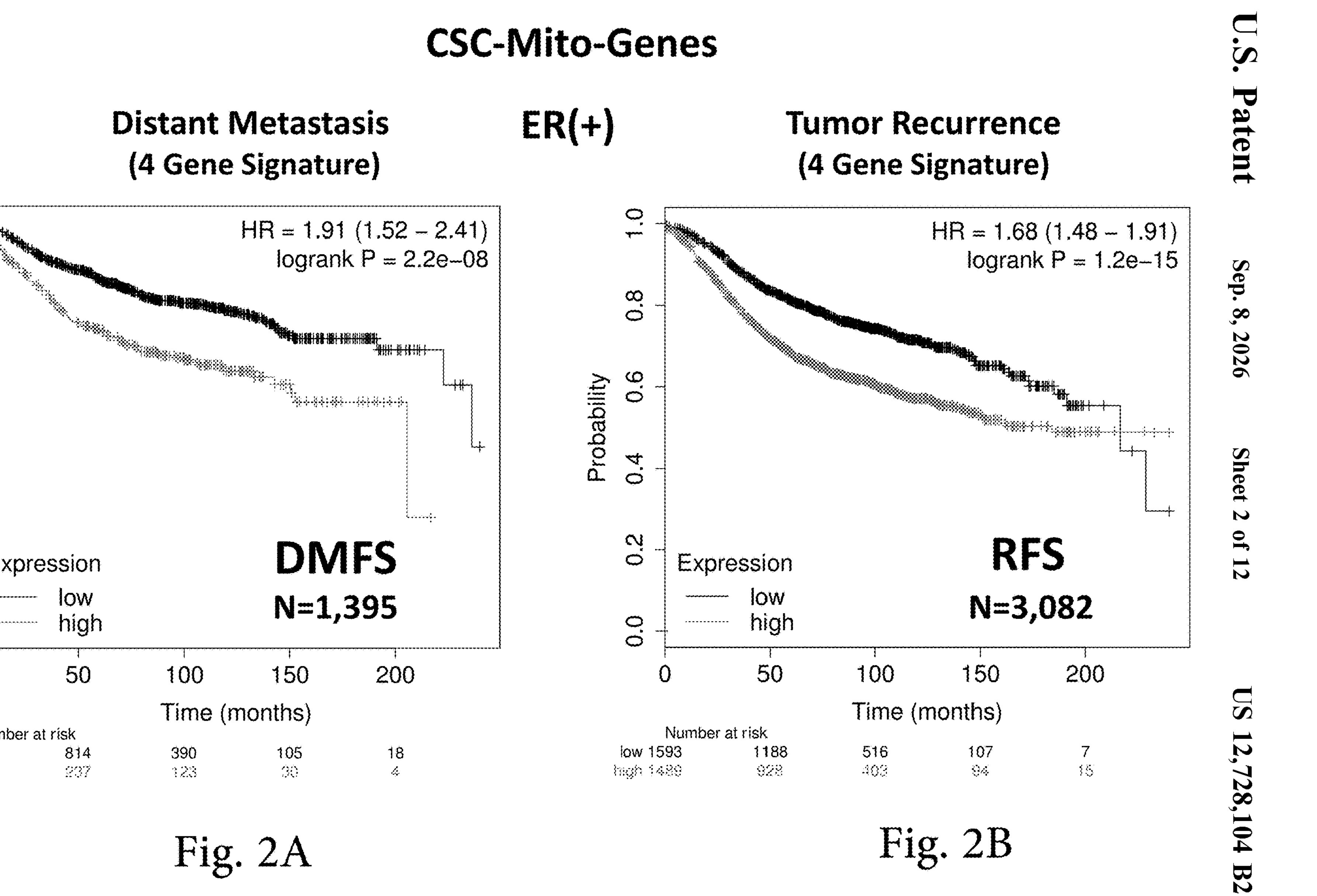
FIGS. 2A and 2B show Kaplan-Meier curves for the CSC-based mitochondrial 4-gene signature of ACLY, VDAC3, HADH2, and COX6B1, for distant metastasis and recurrence, respectively.

FIGS. 2A and 2B show Kaplan-Meier curves for the CSC-based mitochondrial 4-gene signature of ACLY, VDAC3, HADH2, and COX6B1, for distant metastasis and recurrence, respectively. As can be seen, the 4-gene signature predicts distant metastasis and tumor recurrence in ER(+) breast cancer patients. The 4-gene signature shows an increased prognostic value, related to distant metastasis (HR=1.91; P=2.2e−08), and also is able to predict tumor recurrence in the same patient population (HR=1.68; P=1.2e−15). These CSC-based mitochondrial signatures may provide a new prognostic approach for predicting treatment failure in breast cancer patients.

The data demonstrate that these CSC-based mitochondrial signatures provide a new prognostic approach for predicting distant metastasis and tumor recurrence in breast cancer patients. Most importantly, these results also biologically and functionally implicate CSC mitochondria in the process of metastasis and tumor recurrence. The gene signatures described herein may be used to identify candidates for treatment with mitochondrial inhibitors, i.e., mitochondrial inhibition therapy. As one having an ordinary level of skill in the art will appreciate, a candidate showing over-expression of the genes in the gene signatures above are more likely to benefit from mitochondrial inhibition therapy. The following paragraphs describe examples of mitochondrial inhibitors that may be used in candidates for mitochondrial inhibition therapy.

To functionally evaluate the role of mitochondria in cancer metastasis, the inventors used a series of mitochondrial inhibitors that were previously developed to specifically target the propagation of CSCs, known as Mitoriboscins. These inhibitors were developed via in silico screening of a library of 45,000 compounds, to identify positive hits that bound to the 3D-structure of the large mitochondrial ribosome. After 880 positive hits were identified, these compounds were then subjected to phenotypic drug screening, using an ATP-depletion assay, and directly validated using the Seahorse Metabolic Flux analyser, to confirm their specificity as bona fide mitochondrial inhibitors. Ultimately, this screening approach led to the identification of three major compounds, known as 23/G4, 24/D4 and 24/F9, which all inhibited 3D-mammosphere formation in MCF7 cells and significantly blocked cell migration in MDA-MB-231 cells, all in the low micro-molar range. The structures of 23/G4, 24/D4 and 24/F9 are repeated below, with associated IUPAC chemical names.

23/G4

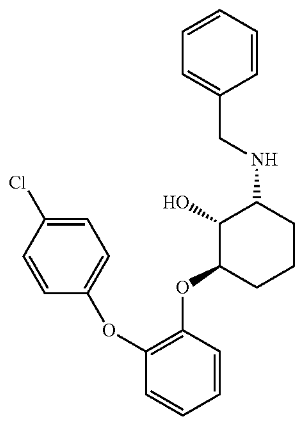

(1R,2R,6R,)-2-(benzylamino)-6-[2-(4-chlorophenoxy)phenoxy]cyclohexanol

24/D4

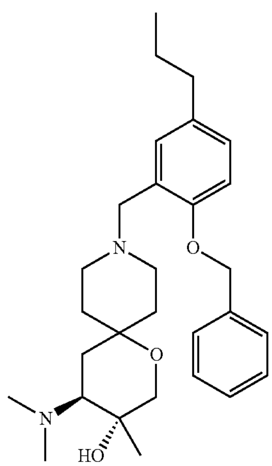

(4S)-1-[(2-benzyloxy-5-chloro-phenyl)methyl]-5-[(1R)-4-methyl-1,4diazepan-1-yl]azepan-4-ol

24/F9

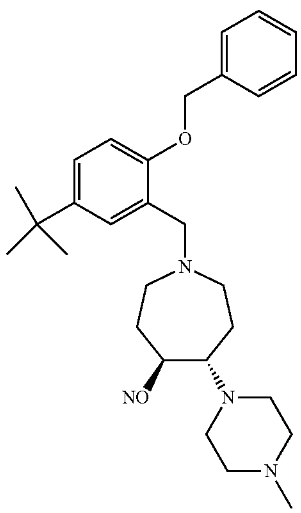

(4S)-1-[(2-benzyloxy-5-tert-butyl-phenyl)methyl]-5-(4-methylpiperazin-1-yl) azepan-4-ol -continued

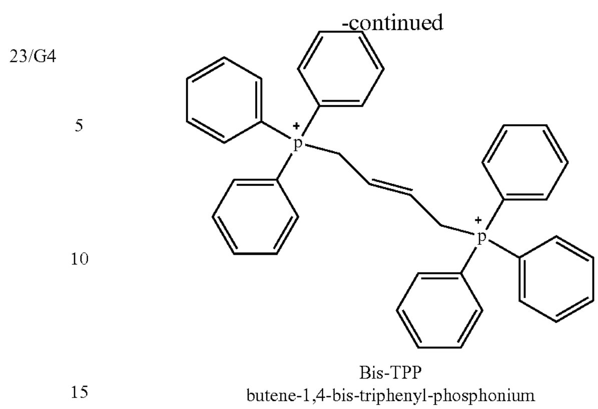

Bis-TPP
butene-1,4-bis-triphenyl-phosphonium

To experimentally evaluate their functional effects in vivo, the inventors used MDA-MB-231 cells and the well-established chorio-allantoic membrane (CAM) assay in chicken eggs, to quantitatively measure tumor growth and metastasis. An inoculum of $1\times10^6$ MDA-MB-231 cells was added onto the CAM of each egg (day E9) and then eggs were randomized into groups. On day E10, tumors were detectable and they were then treated daily for 8 days with vehicle alone (1% DMSO in PBS) or the three Mitoriboscin compounds. In parallel, the inventors also evaluated the activity of another mitochondrial inhibitor, namely butene-1,4-bis-triphenyl-phosphonium (Bis-TPP), which was identified as an inhibitor of 3D-mammosphere formation in MCF7 cells, with an IC-50 of less than 0.5 μM.

Figure 3:
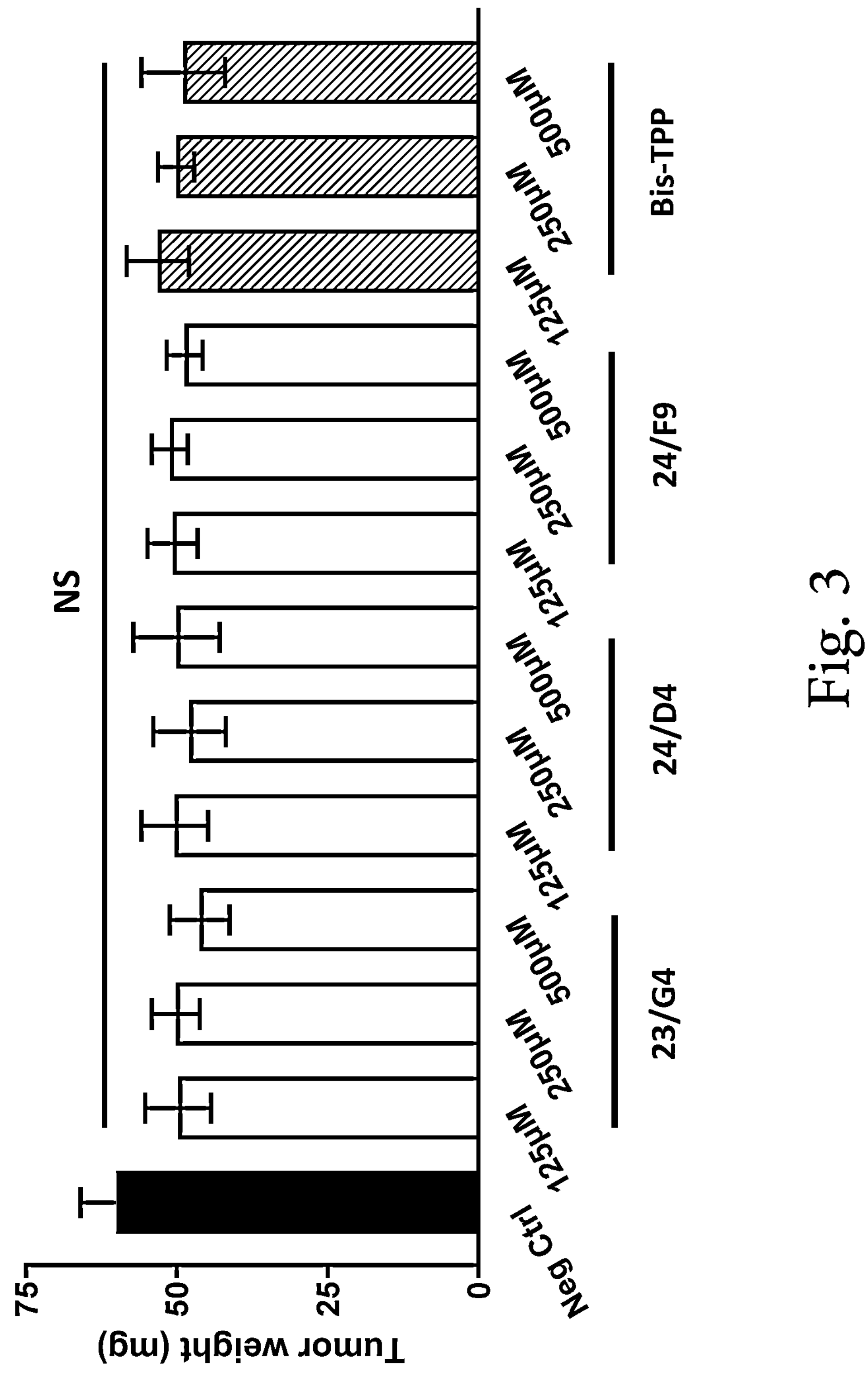
FIG. 3 shows the effects of the three Mitoriboscins (23/G4, 24/D4, 24/F9) and Bis-TPP on MDA-MB-231 tumor growth in the CAM assay.

After 8 days of drug administration (on day E18), all tumors were weighed, and the lower CAM was collected to evaluate the number of metastatic cells, as analyzed by qPCR with specific primers for Human Alu sequences. FIG. 3 shows the effects of the three Mitoriboscins (23/G4, 24/D4, 24/F9) and Bis-TPP on MDA-MB-231 tumor growth in the CAM assay. At the concentrations evaluated, the four inhibitors showed minor effects on tumor growth in the CAM assay, as a result of the 8-day period of drug administration. Note that these results do not indicate that these compounds are ineffective at inhibiting CSCs—the bulk cancer cells are already forming in the CAM assay at the time of drug administering, and further evaluations are planned using increased concentration of the compounds.

Figure 4:
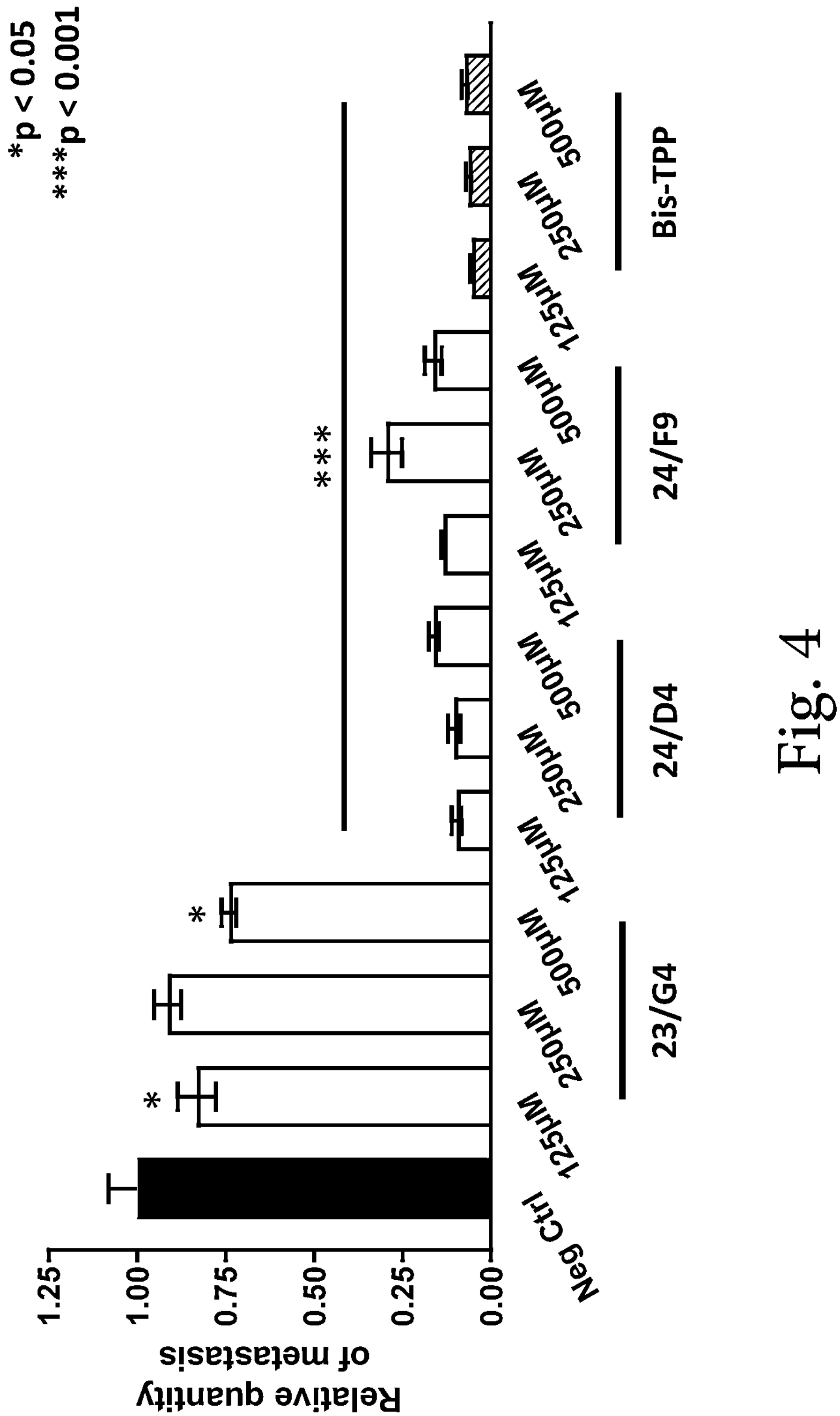
FIG. 4 shows the effects of the three Mitoriboscins (23/G4, 24/D4, 24/F9) and Bis-TPP on MDA-MB-231 metastasis in the CAM assay.

However, all four mitochondrial inhibitors showed significant effects on MDA-MB-231 cancer metastasis. MDA-MB-231 cells and the CAM assay in chicken eggs were used to quantitatively measure spontaneous tumor mestastasis. An inoculum of $1\times10^6$ MDA-MB-231 cells was added onto the CAM of each egg (on day E9) and then eggs were then randomized into groups. On day E10, tumors were detectable and they were then treated daily for 8 days with vehicle alone (1% DMSO in PBS) or the four mitochondrial inhibitors. After 8 days of drug administration, the lower CAM was collected to evaluate the number of metastatic cells, as analyzed by qPCR with specific primers for Human Alu sequences. The results are summarized in FIG. 4. As can be seen, FIG. 4 illustrates that all three Mitoriboscins were clearly effective in inhibiting metastasis. Mitoriboscin compounds 24/D4 and 24/F9 were the most effective of the Mitoriboscins, and Bis-TPP also significantly prevented metastasis. All four mitochondrial inhibitors tested showed significant effects on MDA-MB-231 metastasis. The same procedure may be used to evaluate the anti-metastasis and anti-recurrence effects of other mitochondrial inhibitors.

Figure 5:
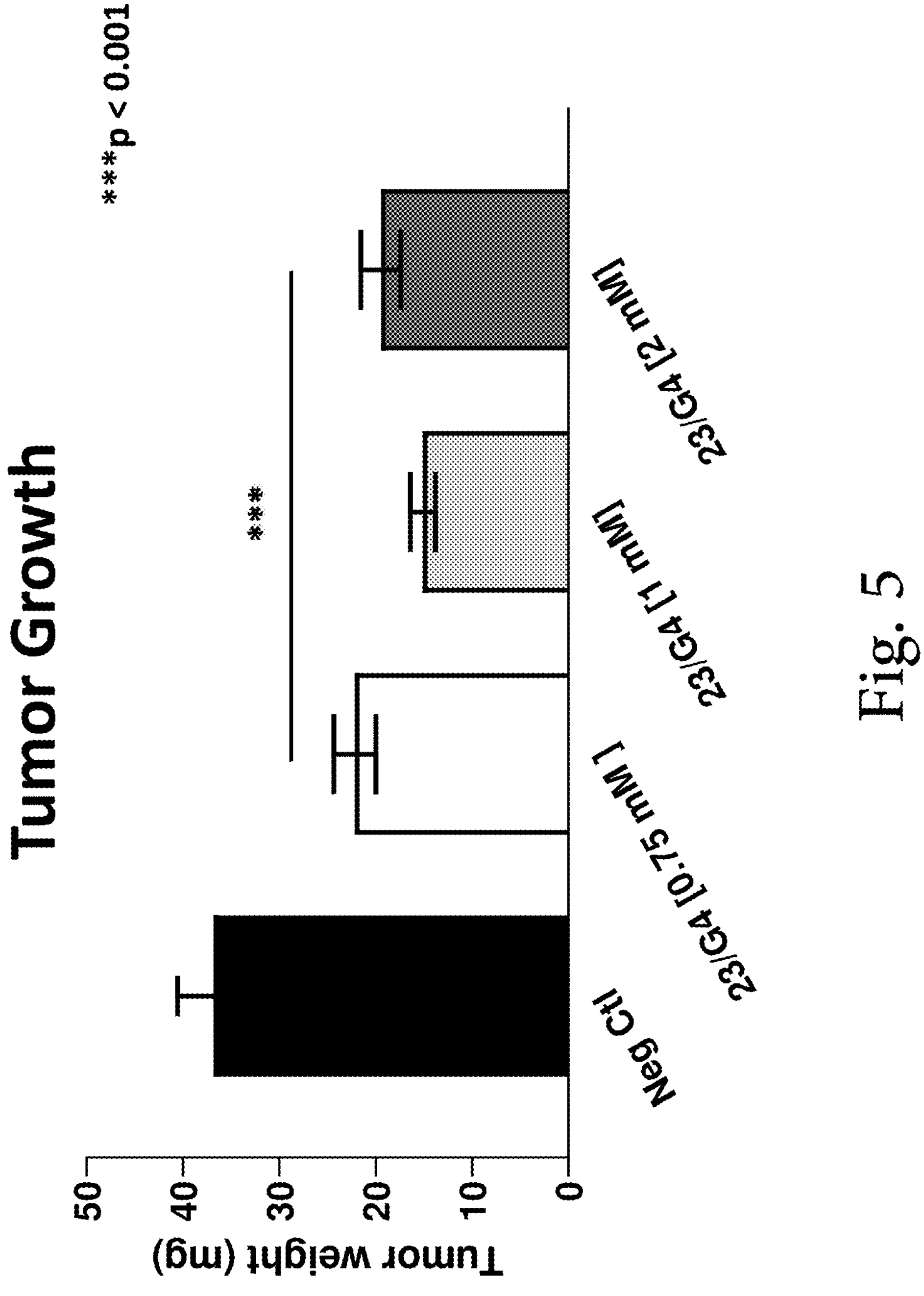
FIG. 5 shows the effects of Mitoriboscin compound 23/G4 on tumor growth.
Figure 6:
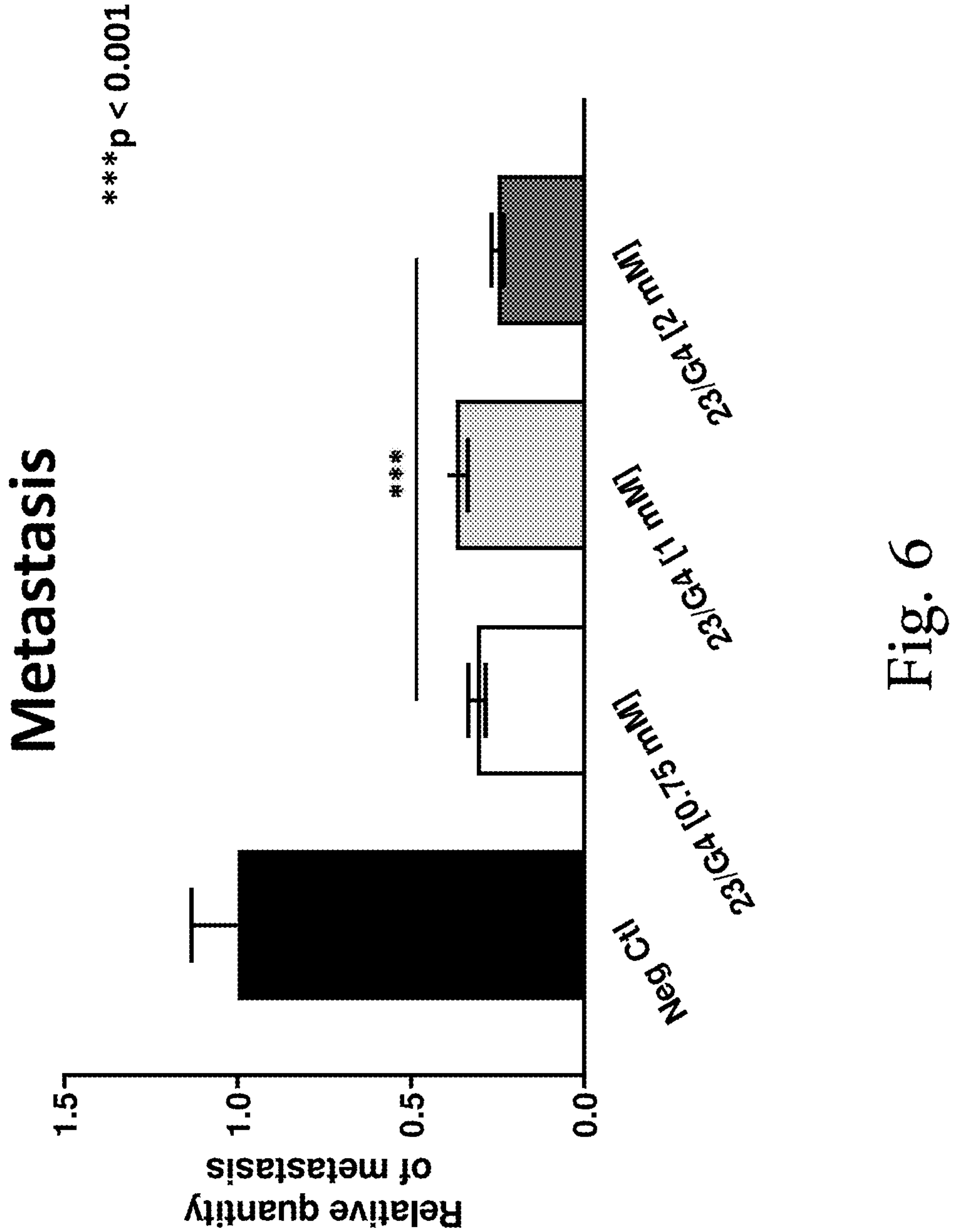
FIG. 6 shows the effects of Mitoriboscin compound 23/G4 on cancer metastasis.

As Mitoriboscin compound 23/G4 was minimally effective at a concentration of 0.5 mM, it was tested at higher concentrations of 0.75 mM, 1 mM, and 2 mM. FIG. 5 shows the effects of Mitoriboscin compound 23/G4 on tumor growth. As can be seen, compound 23/G4 inhibited tumor growth by 40% to 60% at the higher concentrations (averages are shown +SEM. *p<0.001). FIG. 6 shows the effects of Mitoriboscin compound 23/G4 on cancer metastasis. As expected, the effects of compound 23/G4 on metastasis were significantly more pronounced. At the higher concentrations tested, compound 23/G4 significantly inhibited metastasis by about 70-75%. The inhibition effects of compound 23/G4 on metastasis were significantly more pronounced than its effects on tumor growth. Averages are shown +SEM. *p<0.001.

The results show that at the concentrations evaluated, compound 23/G4 significantly inhibited both tumor growth by 40% to 60%, and metastasis by 70-75%. This demonstrates that compound 23/G4, a mitochondrial inhibitor, is suitable for use in the treatment and prevention of tumor recurrence and metastasis.

Additionally, little or no embryo toxicity was observed in these experiments. Otherwise tumor growth and cancer metastasis assays could not have been completed. Tables 4, 5, and 6, below, show the results of embryo toxicity of selected mitochondrial inhibitor compounds. Therefore, the inventors conclude that mitochondrial inhibitors can be used experimentally, to preferentially inhibit tumor metastasis, without significant toxicity.

TABLE 4

Chick Embryo Toxicity of Mitoriboscins and Bis-TPP at a concentration of 0.5 mM.

| Group # | Group Description | Total | Alive | Dead | % Alive | % Dead |
|---|---|---|---|---|---|---|
| 1 | Neg. Ctrl. | 18 | 16 | 2 | 88.89 | 11.11 |
| 2 | 23/G4 | 10 | 7 | 3 | 70 | 30 |
| 3 | 24/D4 | 12 | 12 | 0 | 100 | 0 |
| 4 | 24/F9 | 10 | 8 | 2 | 80 | 20 |
| 5 | Bis-TPP | 12 | 7 | 5 | 58.33 | 41.67 |

TABLE 5

Chick Embryo Toxicity of Mitoriboscin 23/G4 at Higher Concentrations.

| Group # | Group Description | Total | Alive | Dead | % Alive | % Dead |
|---|---|---|---|---|---|---|
| 1 | Neg Ctrl | 17 | 12 | 5 | 70.59 | 29.41 |
| 8 | 23/G4 [0.75 mM] | 14 | 10 | 4 | 71.43 | 28.57 |
| 9 | 23/G4 [1 mM] | 15 | 12 | 3 | 80 | 20 |
| 10 | 23/G4 [2 mM] | 15 | 10 | 5 | 66.67 | 33.33 |

TABLE 6

Chick Embryo Toxicity of Dodecyl-TPP.

| Group # | Group Description | Total | Alive | Dead | % Alive | % Dead |
|---|---|---|---|---|---|---|
| 1 | Neg. Ctrl. | 18 | 13 | 5 | 72.22 | 27.78 |
| 2 | d-TPP [6.25 μM] | 19 | 13 | 6 | 68.42 | 31.58 |
| 3 | d-TPP [25 μM] | 19 | 13 | 6 | 68.42 | 31.58 |
| 4 | d-TPP [62.5 μM] | 19 | 3 | 16 | 15.79 | 84.21 |

Figure 7:
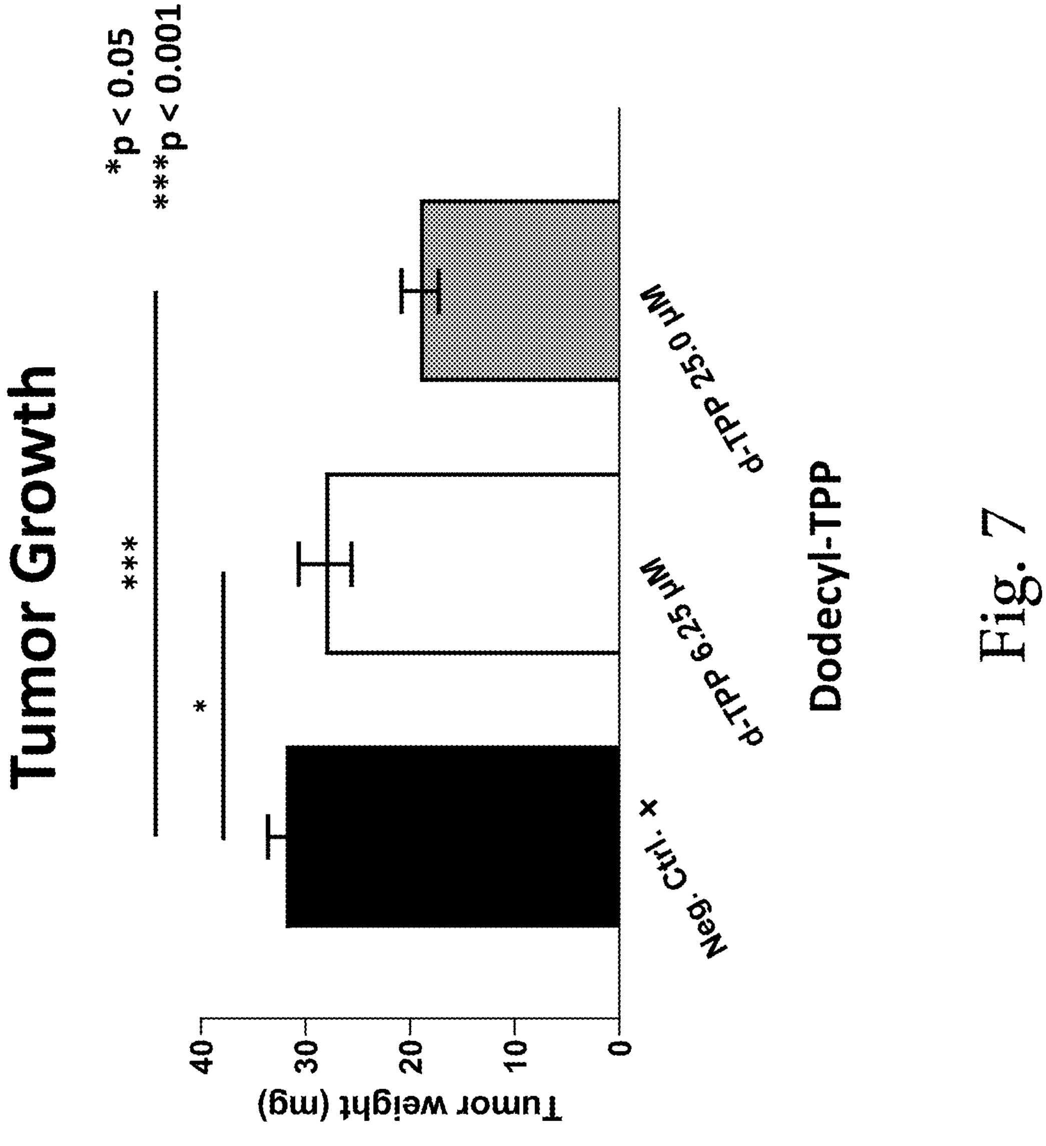
FIG. 7 shows the effects of Dodecyl-TPP on tumor growth.

Another mitochondrial inhibitor, a potent mitochondrially-targeted TPP compound, namely Dodecyl-TPP, was also evaluated using low micro-molar concentrations (6.25 μM and 25 μM). FIG. 7 shows the effects of Dodecyl-TPP on tumor growth. Dodecyl-TPP significantly inhibited tumor growth by 12% to 40% (averages are shown ±SEM. *p<0.05; ***p<0.001). The structure of Dodecyl-TPP (d-TPP) is below. Note the 12-carbon alkyl-chain attached to the lipophilic cation, triphenyl-phosphonium (TPP).

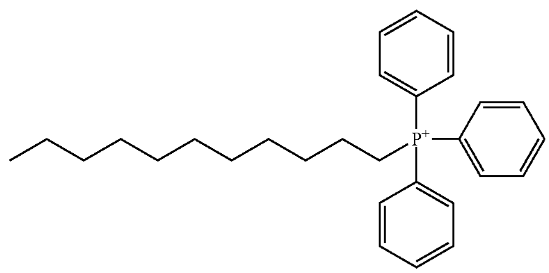

Dodecyl-TPP

Figure 8:
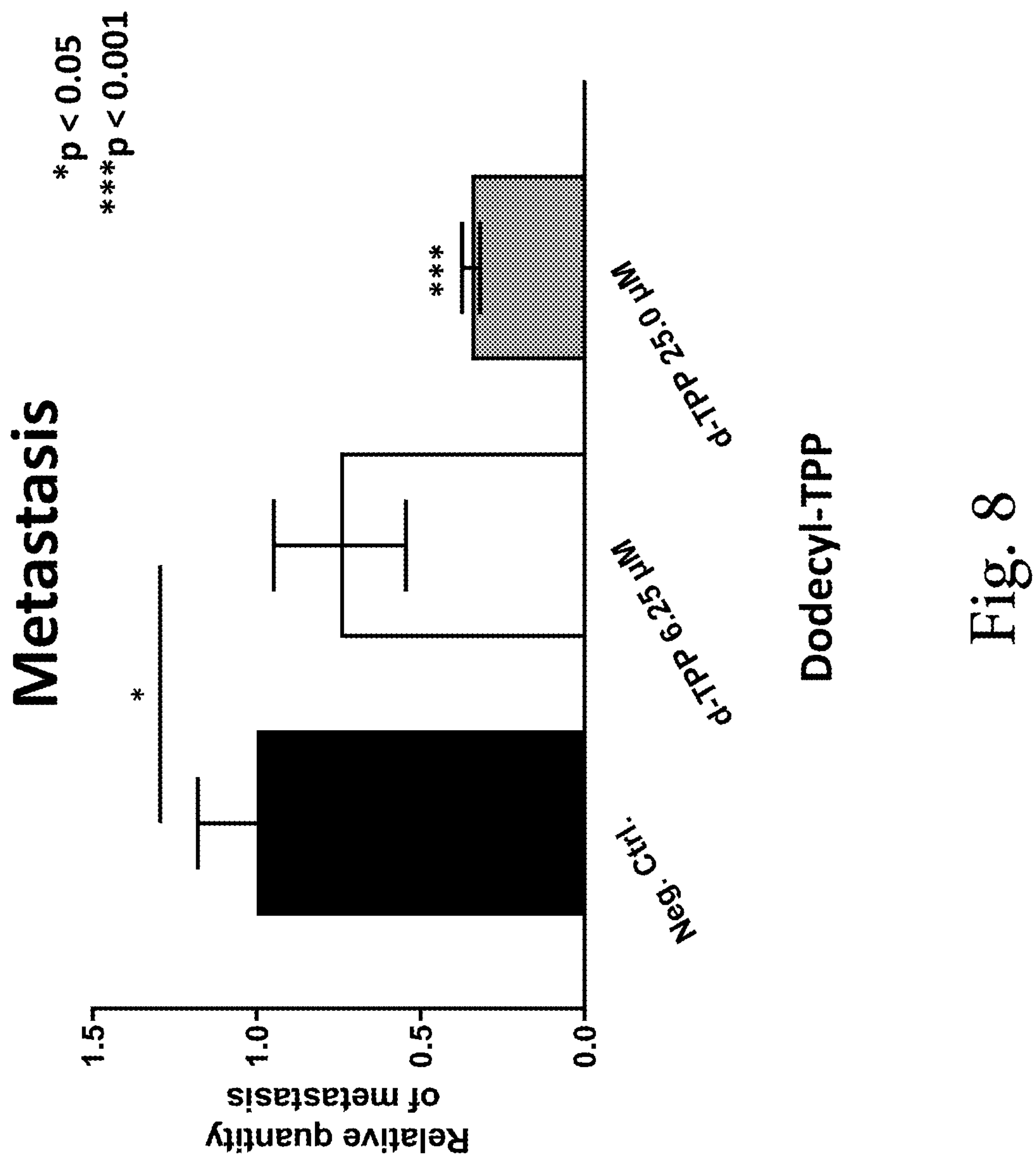
FIG. 8 shows the effects of Dodecyl-TPP on cancer metastasis, at the same micro-molar concentrations.

FIG. 8 shows the effects of Dodecyl-TPP on cancer metastasis, at the same micro-molar concentrations. As can be seen, Dodecyl-TPP significantly inhibited metastasis by 25% to 65% (averages are shown +SEM. *p<0.05; ***p<0.001). Little or no toxicity was observed for Dodecyl-TPP at 6.25 μM and 25 μM, as evident from Table 6, above. As predicted, Dodecyl-TPP preferentially targeted metastasis, rather than tumor growth. Dodecyl-TPP showed some toxicity 62.5 μM, preventing reliable analysis of its effects on tumor growth and metastasis, at this higher concentration.

Given the functional effects of the Mitoriboscin compounds on metastasis, the inventors also evaluated if the gene mRNA transcripts of the large mitochondrial ribosomal proteins (MRPL) show any prognostic value in ER(+) and ER(−)/basal breast cancer patients. In ER(+) breast cancer, a 9-gene mito-ribosome signature was able to effectively predict distant metastasis in N=1,395 patients (HR=1.59; P=5e−05) and tumor recurrence in N=3,082 patients (HR=1.71; P<1e−16). This gene signature included MRPL15, MRPL13, MRPL17, MRPL46, MRPL18, MRPL48, MRPL3, MRPL24, and MRPL4. Table 7, below, shows the results of this 9-gene distant metastasis signature on the prognostic value of large mitochondrial ribosomal proteins, evaluated in ER(+) Breast Cancer Patients (DMFS/ER(+)/N=1,395/>240-months). Table 8, also below, shows the results of the same 9-gene signature for tumor recurrence (RFS/ER(+)/N=3,082/>240-months).

TABLE 7

Distant Metastasis Signature (9 Genes): Prognostic Value of Large Mito-Ribosomal Proteins, Evaluated in ER(+) Breast Cancer Patients (DMFS/ER(+)/N = 1,395/>240-months)

| Probe | Symbol | HR (DMFS) | Log-Rank Test |
|---|---|---|---|
| 218027_at | MRPL15 | 1.68 | 4.1e−06 |
| 218049_s_at | MRPL13 | 1.56 | 8.8e−05 |
| 222216_s_at | MRPL17 | 1.53 | 0.00044 |
| 219244_s_at | MRPL46 | 1.46 | 0.0013 |
| 217907_at | MRPL18 | 1.40 | 0.005 |
| 218281_at | MRPL48 | 1.38 | 0.0078 |
| 208787_at | MRPL3 | 1.37 | 0.0086 |

TABLE 7-continued

Distant Metastasis Signature (9 Genes): Prognostic Value of Large Mito-Ribosomal Proteins, Evaluated in ER(+) Breast Cancer Patients (DMFS/ER(+)/N = 1,395/>240-months)

| Probe | Symbol | HR (DMFS) | Log-Rank Test |
|---|---|---|---|
| 218270_at | MRPL24 | 1.33 | 0.021 |
| 218105_s_at | MRPL4 | 1.29 | 0.023 |
| Combined | | 1.59 | 5e−05 |

TABLE 8

Tumor Recurrence Signature (9 Genes): Prognostic Value of Large Mito-Ribosomal Proteins, Evaluated in ER(+) Breast Cancer Patients (RFS/ER(+)/N = 3,082/>240-months).

| Probe | Symbol | HR (RFS) | Log-Rank Test |
|---|---|---|---|
| 218027_at | MRPL15 | 1.72 | <1e−16 |
| 218049_s_at | MRPL13 | 1.71 | <1e−16 |
| 208787_at | MRPL3 | 1.71 | <1e−16 |
| 222216_s_at | MRPL17 | 1.70 | 1.1e−16 |
| 217907_at | MRPL18 | 1.55 | 2e−11 |
| 218281_at | MRPL48 | 1.26 | 0.00041 |
| 218105_s_at | MRPL4 | 1.24 | 0.00095 |
| 219244_s_at | MRPL46 | 1.21 | 0.0083 |
| 218270_at | MRPL24 | 1.10 | 0.2 |
| Combined | | 1.71 | <1e−16 |

Figures 9A, 9B:
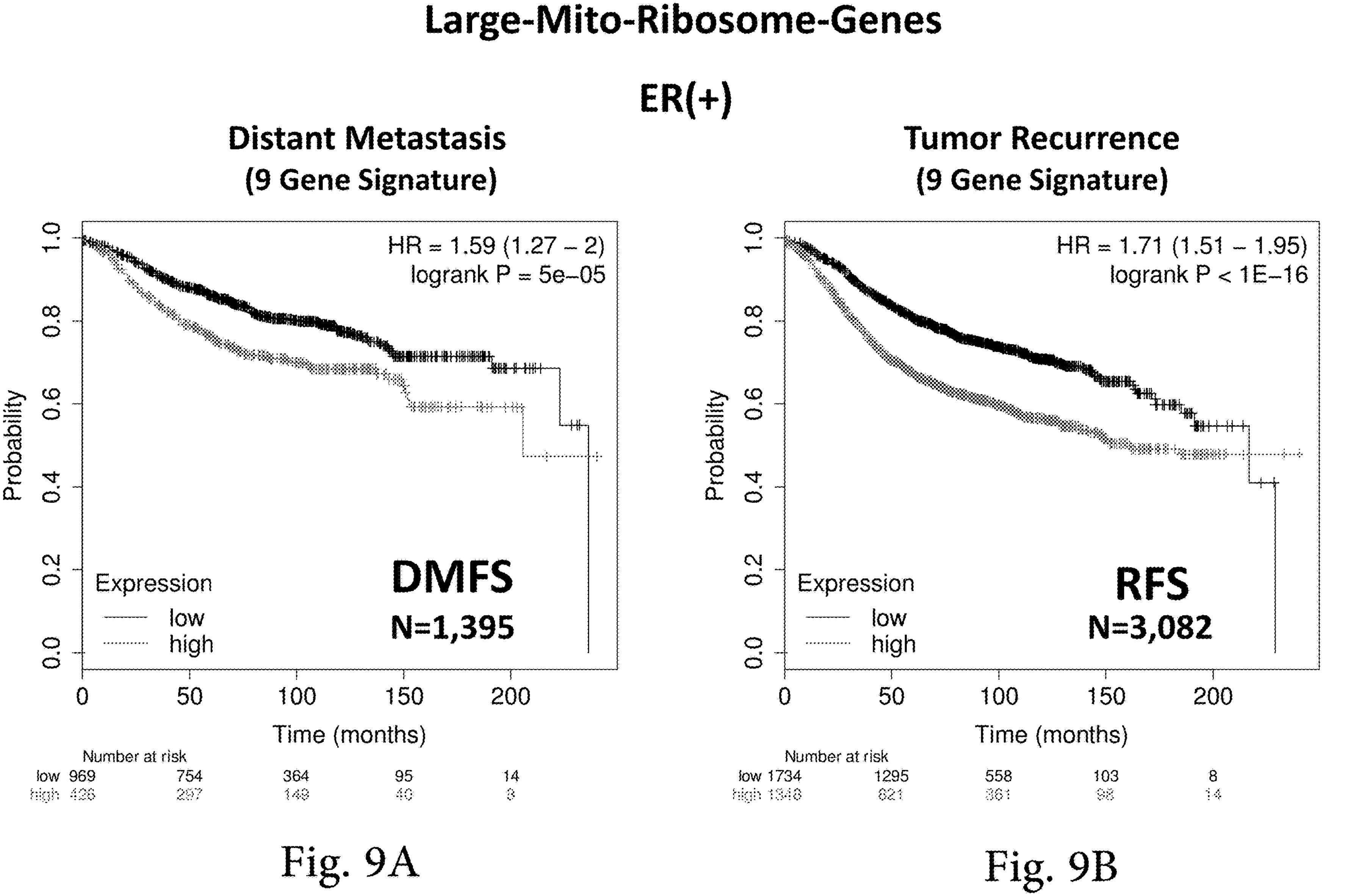
FIGS. 9A and 9B show Kaplan-Meier curves for the 9-gene, large mitochondrial ribosome signature, as a predictor of distant metastasis and tumor recurrence, respectively, in ER(+) breast cancer patients.

FIGS. 9A and 9B show Kaplan-Meier curves for the 9-gene, large mitochondrial ribosome signature, as a predictor of distant metastasis and tumor recurrence, respectively, in ER(+) breast cancer patients. This 9-gene mitochondrial ribosome signature, made up of MRPL15, MRPL13, MRPL17, MRPL46, MRPL18, MRPL48, MRPL3, MRPL24, and MRPL4, effectively predicts distant metastasis in N=1,395 patients (HR=1.59; P=5e−05) and tumor recurrence in N=3,082 patients (HR=1.71; P<1e−16).

A closely related mitochondrial ribosome signature was also able to predict treatment failure in a sub-set of ER(+) patients undergoing Tamoxifen treatment, which resulted in distant metastasis (N=618 patients; HR=2.16; P=1.7e−05) and tumor recurrence (N=799 patients; HR=3.45; P=1.6e−08). This gene signature includes MRPL15, MRPL46, MRPL17, MRPL24, MRPL18, and MRPL13. Table 9, below, shows the prognostic value of this gene signature on metastasis in ER(+) Breast Cancer Patients (DMFS/ER(+)/N=618/>240-months) Treated with Tamoxifen. Table 10, also below, shows the prognostic value of the same gene signature on tumor recurrence in ER(+) Breast Cancer Patients (RFS/ER(+)/N=799/>240-months) Treated with Tamoxifen.

TABLE 9

Distant Metastasis Signature (6 Genes): Prognostic Value of Large Mito-Ribosomal Proteins, Evaluated in ER(+) Breast Cancer Patients (DMFS/ER(+)/N = 618/>240-months) Treated with Tamoxifen.

| Probe | Symbol | HR (DMFS) | Log-Rank Test |
|---|---|---|---|
| 218027_at | MRPL15 | 2.15 | 1.7e−06 |
| 219244_s_at | MRPL46 | 1.99 | 0.00011 |
| 222216_s_at | MRPL17 | 1.99 | 0.0036 |
| 218270_at | MRPL24 | 1.94 | 0.00024 |
| 217907_at | MRPL18 | 1.71 | 0.0051 |
| 218049_s_at | MRPL13 | 1.55 | 0.021 |
| Combined | | 2.16 | 1.7e−05 |

TABLE 10

Tumor Recurrence Signature (8 Genes): Prognostic Value of Large Mito-Ribosomal Proteins, Evaluated in ER(+) Breast Cancer Patients (RFS/ER(+)/N = 799/>240-months) Treated with Tamoxifen.

| Probe | Symbol | HR (RFS) | Log-Rank Test |
|---|---|---|---|
| 218027_at | MRPL15 | 2.20 | 7.8e−08 |
| 208787_at | MRPL3 | 2.04 | 0.00015 |
| 222216_s_at | MRPL17 | 2.01 | 2.3e−06 |
| 217907_at | MRPL18 | 1.92 | 9.1e−06 |
| 218270_at | MRPL24 | 1.77 | 0.00012 |
| 218049_s_at | MRPL13 | 1.66 | 0.0059 |
| 218281_at | MRPL48 | 1.55 | 0.0033 |
| 219244_s_at | MRPL46 | 1.53 | 0.0063 |
| Combined | | 3.45 | 1.6e−08 |

Figures 10A, 10B:
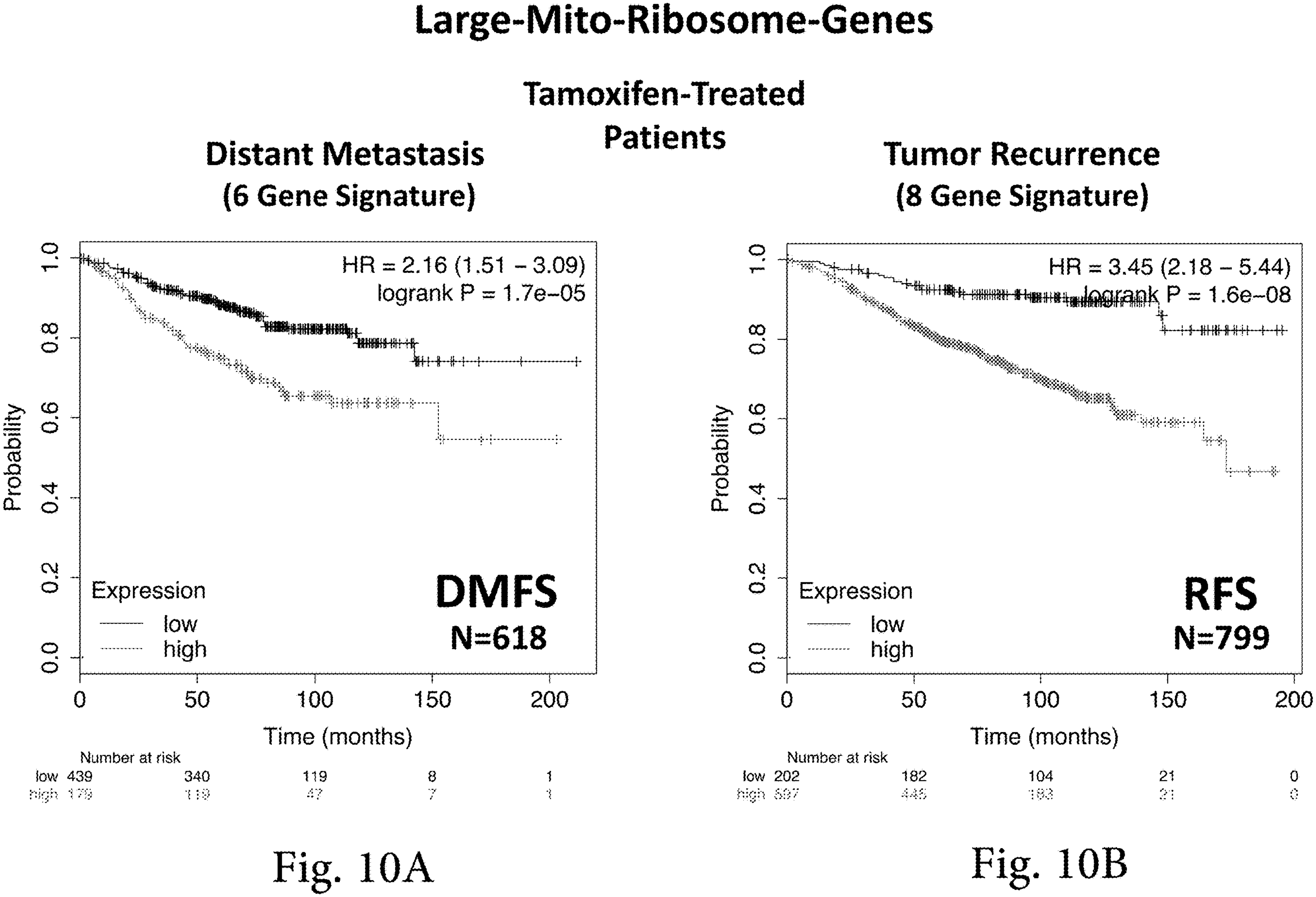
FIGS. 10A and 10B show Kaplan-Meier curves demonstrating that this large mito-ribosome gene signature predicts distant metastasis and tumor recurrence, respectively, in ER(+) breast cancer patients, treated with Tamoxifen.

FIGS. 10A and 10B show Kaplan-Meier curves demonstrating that this large mito-ribosome gene signature predicts distant metastasis and tumor recurrence, respectively, in ER(+) breast cancer patients, treated with Tamoxifen. In this example, the mitochondrial ribosome signature predicts treatment failure in a sub-set of ER(+) patients undergoing Tamoxifen treatment, which resulted in distant metastasis (N=618 patients; HR=2.16; P=1.7e−05) and tumor recurrence (N=799 patients; HR=3.45; P=1.6e−08).

In ER(−)/basal breast cancer, a distinct 6-gene mito-ribosome MRPL signature was able to effectively predict distant metastasis in N=145 patients (HR=2.95; P=0.0018) and tumor recurrence in N=360 patients (HR=2.19; P=1.9e−06), as well as overall survival in N=153 patients (HR=3.17; P=0.00033). This signature includes MRPL42, MRPL41, MRPL54, MRPL13, MRPL36, and MRPL22. Table 11, below, provides the results showing the prognostic value of this signature for distant metastasis in in ER(−)/Basal Breast Cancer Patients (DMFS/N=145/>120-months).

TABLE 11

Distant Metastasis Signature (6 Genes): Prognostic Value of Large Mito-Ribosomal Proteins, Evaluated in ER(−)/Basal Breast Cancer Patients (DMFS/N = 145/>120-months).

| Probe | Symbol | HR (DMFS) | Log-Rank Test |
|---|---|---|---|
| 222466_s_at | MRPL42 | 4.00 | 0.0024 |
| 227186_s_at | MRPL41 | 3.43 | 0.0023 |
| 225797_at | MRPL54 | 2.44 | 0.011 |
| 218049_s_at | MRPL13 | 2.23 | 0.0022 |
| 224331_s_at | MRPL36 | 2.13 | 0.036 |
| 218339_at | MRPL22 | 1.75 | 0.029 |
| Combined | | 2.95 | 0.0018 |

Figures 11A, 11B:
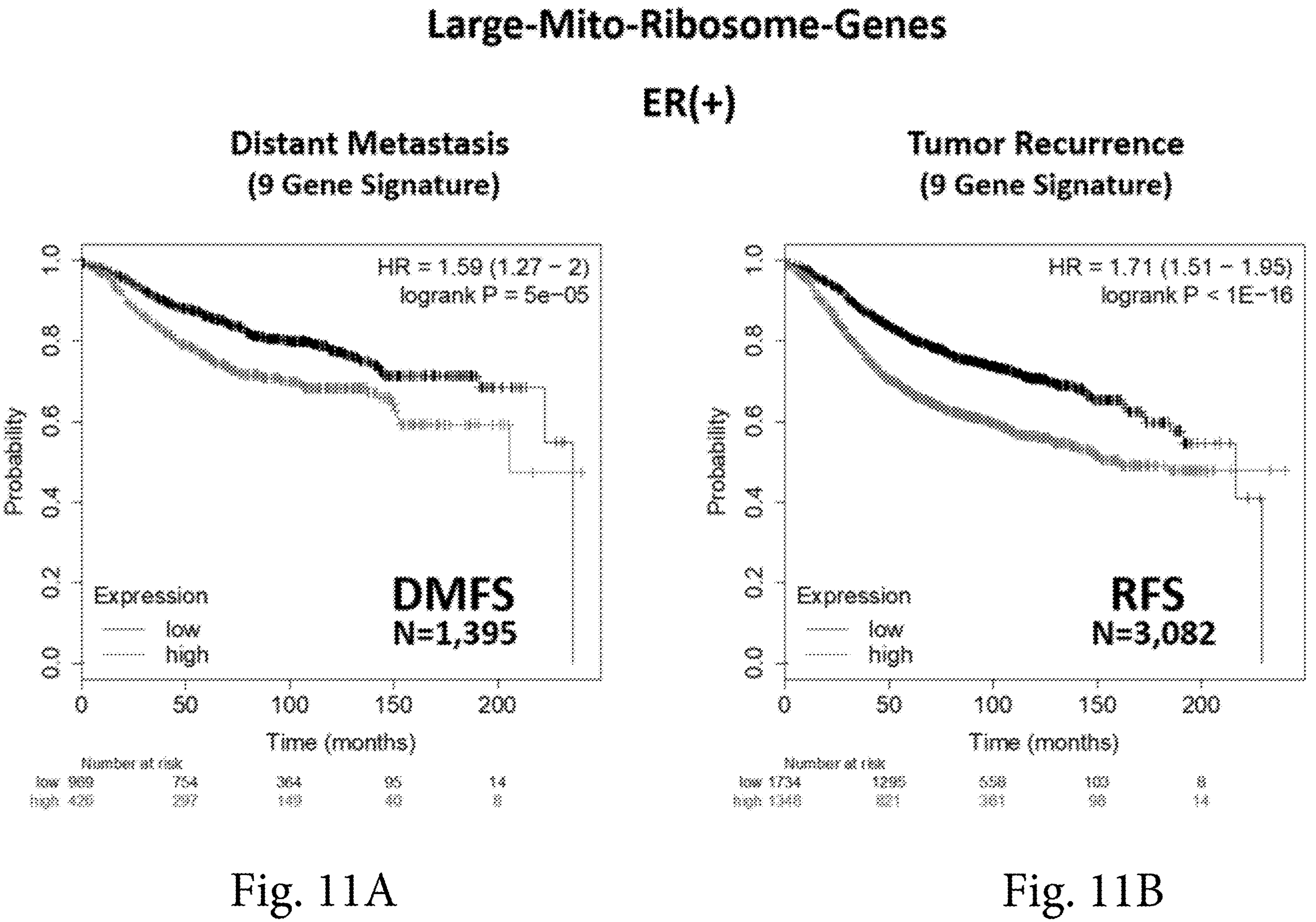
FIGS. 11A and 11B show the Kaplan-Meier curves for the 6-gene, large mitochondrial ribosome gene signature for predicting distant metastasis and tumor recurrence, respectively, in ER(−)/basal breast cancer patients.

FIGS. 11A and 11B show the Kaplan-Meier curves for the 6-gene, large mitochondrial ribosome gene signature for predicting distant metastasis and tumor recurrence, respectively, in ER(−)/basal breast cancer patients. In ER(−)/basal breast cancer, the 6-gene mitochondrial ribosome signature was also able to effectively predict distant metastasis in N=145 patients (HR=2.95; P=0.0018) and tumor recurrence in N=360 patients (HR=2.19; P=1.9e−06).

Figure 12:
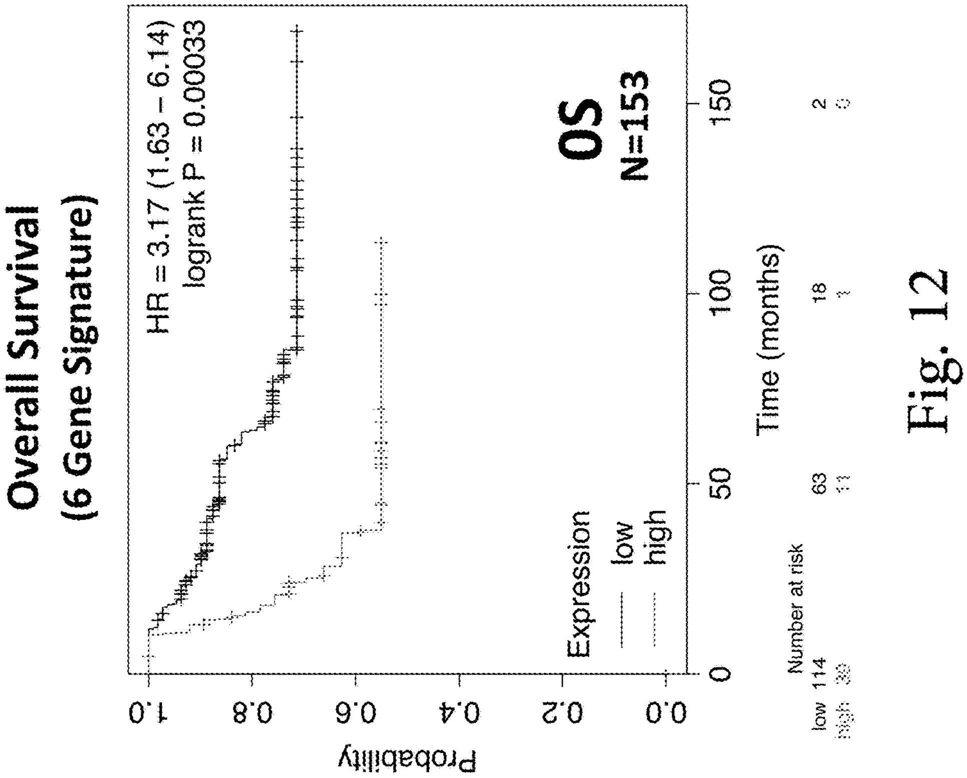
FIG. 12 shows the Kaplan-Meier curves for the 6-gene signature for predicting overall survival in ER(−)/basal breast cancer patients.

The same 6-gene signature may also be used as a predictor of overall survival in ER(−)/basal breast cancer patients. FIG. 12 shows the Kaplan-Meier curves for the 6-gene signature for predicting overall survival in ER(−)/basal breast cancer patients. In ER(−)/basal breast cancer, the 6-gene mitochondrial ribosome signature was also able to effectively predict overall survival in N=153 patients (HR=3.17; P=0.00033).

It should be apparent from the data that these short mitochondrial ribosome gene signatures may be useful as companion diagnostics, to assess which patient populations may benefit most from the administration of mitochondrial inhibitor compounds. Given the impact of mitochondrial inhibitors on metastasis and recurrence, patients having elevated expression of the genes in a particular signature disclosed above are candidates for mitochondrial inhibition therapy. A biological epithelial sample of the cancer may be obtained, and the level of each biomarker in the selected gene signature of the biological sample may be determined. The determined level is compared to a threshold level for each biomarker in the signature, and a pharmaceutically effective amount of a mitochondrial biogenesis inhibitor is administered if the determined levels of the biomarkers in the gene signature exceed the threshold level. Preferably, the mitochondrial biogenesis inhibitor is administered if the determined level for all three biomarkers exceeds the threshold level. The threshold level for each biomarker in the Mito-Signature may be determined using a non-cancerous epithelial sample from the same subject If a patient exhibits elevated expression of the genes in a signature, then the patient may receive a pharmaceutically-effective amount of a mitochondrial inhibitor, such as the Mitoriboscin compounds described herein, Bis-TPP, or Dodecyl-TPP, as non-limiting examples.

Mitochondrial inhibition is an effective strategy for inhibiting cancer recurrence and metastasis, and for eradicating cancer cells and CSCs in particular. A number of categories of mitochondrial inhibitors may be used in connection with the present approach.

A first category of mitochondrial inhibitors are Mitoriboscins, as described above and in U.S. Pat. No. 10,512,618, issued Dec. 24, 2019 and incorporated by reference in its entirety.

A second category of mitochondrial inhibitors include combination therapies involving oxidative metabolism inhibitors and glycolytic metabolism inhibitors. International Application No. PCT/US2018/028587, filed Apr. 20, 2018 and published as WO 2018/195434-A1, is incorporated by reference in its entirety. Some therapies may involve a triple combination having a first antibiotic inhibiting the large mitochondrial ribosome (such as, for example, members of the erythromycin family), a second antibiotic inhibiting the small mitochondrial ribosome (such as, for example, members of the tetracycline family), administered with a pro-oxidant or an agent inducing mitochondrial oxidative stress (e.g., low concentrations of Vitamin C, radiation therapy, among other examples). International Application No. PCT/US2018/028587, filed Dec. 16, 2019, incorporated by reference in its entirety, describes further examples.

A third category of mitochondrial inhibitors, antimitoscins, are described in International Patent Application PCT/US2018/033466, filed May 18, 2018, and incorporated by reference in its entirety. A fourth category of mitochondria biogenesis inhibitors are mitoketoscins, non-carcinogenic compounds that bind to at least one of ACAT1/2 and OXCT1/2 and inhibit mitochondrial ATP production. These compounds are described more fully in International Application PCT/US2018/039354, filed Jun. 25, 2018, incorporated by reference in its entirety. Mitoflavoscins and mitoflavins are a fifth category of mitochondrial biogenesis inhibitors that may be used under the present approach. These compounds are described more fully in International Patent Application PCT/US2018/057093, filed Oct. 23, 2018 and incorporated by reference in its entirety. Mitoflavoscins are compounds that bind to flavin-containing enzymes and inhibit mitochondrial ATP production. Diphenyleneiodonium chloride (DPI) is an example of a mitoflavoscin. A sixth category of mitochondria biogenesis inhibitors are TPP-derivative compounds that show not only a strong preference for uptake in cancer cells (bulk cancer cells, cancer stem cells, and energetic cancer stem cells), but also disrupt mitochondrial biogenesis in these cells. These TPP-derivative compounds are described more fully in International Patent Application PCT/US2018/062174, filed Nov. 21, 2018, which is incorporated by reference in its entirety.

Repurposcins are a seventh category of mitochondrial inhibitors that may be used in embodiments of the present approach. International Patent Application PCT/US2018/062956, filed Nov. 29, 2018 and incorporated by reference in its entirety, describes these compounds more fully. In some embodiments, the inhibitor compound may be a myristol derivative of 9-amino-Doxycycline. For example, the inhibitor compound may have the general formula:

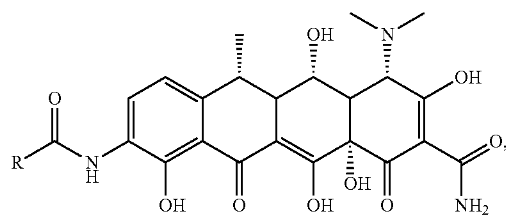

wherein R comprises a C4-C18 alkyl, or a pharmaceutically acceptable salt thereof. For example, in a preferred embodiment, R is 13. An eighth category of mitochondrial inhibitors that may be used in the present approach are MDIVI-1 derivatives, as described in International Patent Application PCT/US2018/066247, filed Dec. 18, 2018 and incorporated by reference in its entirety. Mitochondrial division inhibitor-1 (mDIVI-1) is a small molecule that selectively and reversibly inhibits DRP1. It should be appreciated that other mitochondrial inhibitors may be used, without departing from the present approach.

The following paragraphs describe the materials and methods used in the experiments and results described above. MDA-MB-231 cells, a human breast cancer cell line, were obtained from the American Type Culture Collection (ATCC).

Kaplan-Meier (K-M) analyses: To perform K-M analysis on gene transcripts, the inventors used an open-access online survival analysis tool to interrogate publically available microarray data from up to 3,951 breast cancer patients (18). This allowed the inventors to determine their prognostic value. For this purpose, the inventors primarily analyzed data from ER(+)s and ER(−)/basal patients. Biased array data were excluded from the analysis. This allowed us to identify mitochondrial gene transcripts, with significant prognostic value. Hazard-ratios were calculated, at the best auto-selected cut-off, and p-values were calculated using the Log-rank test and plotted in R. K-M curves were also generated online using the K-M-plotter (as high-resolution TIFF files), using univariate analysis: https://kmplot.com/analysis/index.php?p=service&cancer=breast This approach allowed us to directly perform in silico validation of these mitochondrial biomarker candidates. The multi-gene classifier function of the program was used to test the prognostic value of short mitochondrial gene signatures, using the mean expression of the selected probes. The latest 2020 version of the database was utilized for all these analyses.

Assays for Tumor Growth, Metastasis and Embryo Toxicity:

a) Preparation of Chicken Embryos. Fertilized White Leghorn eggs were incubated at 37.5° C. with 50% relative humidity for 9 days. At that moment (E9), the chorioallantoic membrane (CAM) was dropped down by drilling a small hole through the eggshell into the air sac, and a 1 $cm^2$ window was cut in the eggshell above the CAM (19-23).

b) Amplification and Grafting of Tumor Cells. The MDA-MB-231 tumor cell line was cultivated in DMEM medium supplemented with 10% FBS and 1% penicillin/streptomycin. On day E9, cells were detached with trypsin, washed with complete medium and suspended in graft medium. An inoculum of $1\times10^6$ cells was added onto the CAM of each egg (E9) and then eggs were randomized into groups (19-23).

c) Tumor Growth Assays: At day 18 (E18), the upper portion of the CAM was removed from each egg, washed in PBS and then directly transferred to paraformaldehyde (fixation for 48 h) and weighed (19-23).

d) Metastasis Assays. On day E18, a 1 $cm^2$ portion of the lower CAM was collected to evaluate the number of metastatic cells in 8 samples per group (n=8). Genomic DNA was extracted from the CAM (commercial kit) and analyzed by qPCR with specific primers for Human Alu sequences. Calculation of Cq for each sample, mean Cq and relative amounts of metastases for each group are directly managed by the Bio-Rad® CFX Maestro software. A one-way ANOVA analysis with post-tests was performed on all the data (19-23).

e) Embryo Tolerability Assay: Before each administration, the treatment tolerability was evaluated by scoring the number of dead embryos.

The present approach provides gene signatures and uses thereof as a diagnostic or prognostic platform for use in conjunction with cancer treatments and therapies, to identify candidates for mitochondrial inhibitor therapy. Some embodiments may take the form of a companion diagnostic, such as a diagnostic assay or test in an assayable format. Example formats include a microarray or multiplex arrangement of detectable probes or ligands. A companion diagnostic involving one or more of the unique gene signatures described herein, may be used as indicative of gene expression profiles of a patient's cancer or tumor samples that may be sensitive to mitochondrial inhibitor therapy. The present approach thus provides guidance about how a patient may respond to mitochondrial inhibitor therapy, and in particular how the patient's likelihood of cancer recurrence or transmission will respond to mitochondrial inhibitor therapy. It should be appreciated that in methods of treating, diagnosing, or prognosing a patient's candidacy for mitochondrial inhibitor therapy, assaying or testing a patient's cancer or tumor sample for the expression of genes in one or more of the disclosed gene signatures may be followed by administering a mitochondrial inhibitor to the patient if differential expression of the genes within one or more of the disclosed gene signatures, relative to a control, is detected.

It should be appreciated by those having an ordinary level of skill in the art that the control may depend on the type of sample and assay, and therefore the present approach is not intended to be limited to a particular control. For example, whether the sample is isolated tumor cells or tumor tissue biopsy sample, the type of assay performed. The control may vary depending on such factors. For example, a control can include an assay of normal or non-cancer cells from the patient, or from non-cancer patients. In some embodiments, normalization, particularly for microarray assay platforms, may be performed to adjust for effects arising from variation in the microarray technology, rather than from biological differences between the samples, such as RNA samples, or between the addressable probes.

It should be appreciated that a gene signature expression profile can be prepared directly from a cancer patient's tumor samples or specimens. This may include, for example, extracting or isolating nucleic acid, such as RNA (mRNA), or encoded protein, directly from the tumor samples or specimens (e.g., biopsied samples and specimens) and assaying for the differential expression of genes in the gene signatures, or proteins encoded therefrom. A determination of differential expression of the gene signature genes, or encoded protein, compared to a control, indicates whether the patient is a candidate for mitochondrial inhibitor therapy. The resulting gene signature expression profile, whether prepared directly from a patient's cancer or tumor specimen or prepared from cells derived or cultured therefrom, contains transcript levels or expression levels of genes in the gene signatures of the invention, or encoded proteins thereof, that predict sensitivity of a cancer or tumor to mitochondrial inhibitor therapy, and more particularly, sensitivity of the likelihood of tumor recurrence or metastasis to mitochondrial inhibitor therapy. In some embodiments, an increased differential expression of the genes in the gene signature, relative to a control, indicates that the patient is a candidate for mitochondrial inhibitor therapy.

Some embodiments may take the form of a method in which a gene expression dataset (e.g., a list of gene expression levels) having a gene expression level for each gene in one or more of the disclosed gene signatures, is obtained. The expression levels of the genes in the dataset are compared to gene expression levels of the same genes in a control. The difference in the gene expression level of the genes in the dataset compared with the control gene expression level of the same genes, if any, is calculated. Then, the patient may be identified as a candidate for mitochondrial inhibitor therapy if there is a difference in the dataset expression levels compared to the control expression levels of the same genes, or to the normalized value, for example, if the sensitivity score or cutoff value of the expression of genes in the dataset is above a threshold or cutoff value.

A pharmaceutically effective amount of a mitochondrial inhibitor may be administered to candidates for mitochondrial inhibitor therapy may. The following paragraphs describe pharmaceutical compositions and mitochondrial inhibitor treatment. This disclosure is not intended to be limited to a specific pharmaceutical formulation or pharmaceutically effective amount, at least because the effective amount depends on the mitochondrial inhibitor selected. The inventors consider these variables to be within the ordinary skill in the art, and that the routine experimentation needed to determine the pharmaceutically effective amount is not undue experimentation. With respect to a mitochondrial inhibitor compound, the demonstrative inhibitor compounds are available in various forms. For example, a Mitoriboscin compound or a Bis-TPP or d-TPP, the compound can be administered orally as a solid or as a liquid. In some embodiments, the mitochondrial inhibitor can be administered intramuscularly, intravenously, or by inhalation as a solution, suspension, or emulsion. In some embodiments, mitochondrial inhibitor (which, for the avoidance of doubt, includes salts thereof) can be administered by inhalation, intravenously, or intramuscularly as a liposomal suspension. When administered through inhalation the active compound or salt can be in the form of a plurality of solid particles or droplets having any desired particle size, and for example, from about 0.001, 0.01, 0.1, or 0.5 microns, to about 5, 10, 20 or more microns, and optionally from about 1 to about 2 microns. It should be appreciated that the particular form of administration may vary, and that parameters outside of the scope of this disclosure (e.g., manufacturing, transportation, storage, shelf life, etc.) may be determinative of the common forms and concentrations of the mitochondrial inhibitor compound.

Pharmaceutical compositions of the present approach include a mitochondrial inhibitor (including salts thereof) as an active compound, in any pharmaceutically acceptable carrier. If a solution is desired, water may be the carrier of choice for water-soluble compounds or salts. With respect to water solubility, organic vehicles, such as glycerol, propylene glycol, polyethylene glycol, or mixtures thereof, can be suitable. Additionally, methods of increasing water solubility may be used without departing from the present approach. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized. Embodiments including a second inhibitor compound, such as a glycolysis inhibitor or an OXPHOS inhibitor, may co-administer a form of the second inhibitor available in the art. The present approach is not intended to be limited to a particular form of administration, unless otherwise stated.

In addition to the active compound(s), pharmaceutical formulations of the present approach can contain other additives known in the art. For example, some embodiments may include pH-adjusting agents, such as acids (e.g., hydrochloric acid), and bases or buffers (e.g., sodium acetate, sodium borate, sodium citrate, sodium gluconate, sodium lactate, and sodium phosphate). Some embodiments may include antimicrobial preservatives, such as methylparaben, propylparaben, and benzyl alcohol. An antimicrobial preservative is often included when the formulation is placed in a vial designed for multi-dose use. The pharmaceutical formulations described herein can be lyophilized using techniques well known in the art.

In embodiments involving oral administration of an active compound, the pharmaceutical composition can take the form of capsules, tablets, pills, powders, solutions, suspensions, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc may be included for tableting purposes. Solid compositions of a similar type may be employed as fillers in soft and hard-filled gelatin capsules. Materials in this connection also include lactose or milk sugar, as well as high molecular weight polyethylene glycols. When aqueous suspensions and/or elixirs are desired for oral administration, the compounds of the presently disclosed subject matter can be combined with various sweetening agents, flavoring agents, coloring agents, emulsifying agents and/or suspending agents, as well as such diluents as water, ethanol, propylene glycol, glycerin and various like combinations thereof. In embodiments having d-TPP with a second inhibitor compound, the second inhibitor compound may be administered in a separate form, without limitation to the form of the d-TPP compound.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

With respect to pharmaceutical compositions, the pharmaceutically effective amount of an active compound described herein will be determined by the health care practitioner, and will depend on the condition, size and age of the patient, as well as the route of delivery. In one non-limited embodiment, a dosage from about 0.1 to about 200 mg/kg has therapeutic efficacy, wherein the weight ratio is the weight of the active compound, including the cases where a salt is employed, to the weight of the subject. In some embodiments, the dosage can be the amount of active compound needed to provide a serum concentration of the active compound of up to between about 1 and 5, 10, 20, 30, or 40 μM. In some embodiments, a dosage from about 1 mg/kg to about 10, and in some embodiments about 10 mg/kg to about 50 mg/kg, can be employed for oral administration. Typically, a dosage from about 0.5 mg/kg to 5 mg/kg can be employed for intramuscular injection. In some embodiments, dosages can be from about 1 μmol/kg to about 50 μmol/kg, or, optionally, between about 22 μmol/kg and about 33 mol/kg of the compound for intravenous or oral administration. An oral dosage form can include any appropriate amount of active material, including for example from 5 mg to, 50, 100, 200, or 500 mg per tablet or other solid dosage form, depending on the pharmaceutically effective amount desired.

It should be appreciated that the person having an ordinary level of skill in the art can use methods common and known in the art to develop a formulation for a particular embodiment. In some embodiments, the pharmaceutical composition may be in a tablet, capsule, or pill. The pharmaceutical composition may have a dose of the therapeutic composition from 20 mg to 500 mg. In some embodiments, the pharmaceutical composition may comprise a tablet having 200 mg of the therapeutic compound, e.g., a compound described above, such as compound 23/G4. A tablet may contain a therapeutic compound content of at least about 35%, 40%, 45%, 50% or 55%, measured by w/w percentage of the therapeutic compound (as a free base) of the core tablet.

The tablet may have a core formed of microcrystalline cellulose, crospovidone type A, low-substituted hydroxypropylcellulose, magnesium stearate, colloidal anhydrous silica. In a first demonstrative embodiment, a tablet having 200 mg of the therapeutic compound (e.g., compound 23/G4) may include an inner core having microcrystalline cellulose (67.44 mg), hydroxypropyl cellulose (48.12 mg), crospovidone (29.20 mg), colloidal silicon dioxide (anhydrous) (2.12 mg), and magnesium stearate (6.36 mg), and an outer core having crospovidone (12.84 mg), colloidal silicon dioxide (anhydrous) (1.06 mg), and magnesium stearate (8.46 mg). In a second demonstrative embodiment, a tablet may have from about 10% to about 45% (w/w) of the therapeutic compound (e.g., compound 23/G4), and preferably about 18% to about 28% of the therapeutic compound; from about 4% to about 18% water-soluble acid; from about 20% to about 75% diluent; from about 5% to about 18% disintegrant; from about 0.2% to about 10% lubricant; and, optionally, glidant from about 0% to about 5%, and from about 0% to about 15% binder. It should be appreciated that pharmaceutical compositions of the present approach may closely resemble pharmaceutical compositions including the parent compound.

The tablet may have a film coating. The film coating may include iron oxide black, iron oxide red, soya lecithin, polyvinyl alcohol (partially hydrolysed), talc, titanium dioxide, and xanthan gum. The tablet may be coated using commercially available coating premixes, depending on the desired appearance of the final tablet. For example, persons having Opadry® (Colorcon, Harleysville, PA) is an HPMC (hydroxypropyl-methylcellulose) coating material and has the following composition: HPMC (Pharmacoat 603) 71.4%, polyethylene glycol 7.15%, talc 7.15%, and iron oxide 14.3%.

Methods of treatment described herein are preferably carried out by administering a therapeutically effective amount of a selected compound, to a subject in need of treatment. The candidate subject would express elevated levels of the genes in one of the gene signatures described above. The compounds can be administered by a variety of routes, including orally and parenterally, and have little or no toxicity, as discussed above.

Some embodiments of the present approach may take the form of a kit containing reagents for the detection of genes in at least one of the gene signatures described herein, and optionally instructions for use. The kit may be for predicting a patient's candidacy for mitochondrial inhibitor therapy. Kits according to the present approach may include nucleic acid probes that specifically bind to nucleotide sequences corresponding to genes in one or more of the gene signatures disclosed herein. In some embodiments, kits may include antibodies or ligands that specifically bind to polypeptides or peptides encoded by the genes in one or more of the gene signatures disclosed herein, and a means of labelling the antibodies or ligands that specifically bind to the polypeptides or peptides encoded by the genes. Persons having an ordinary level of skill in the art will appreciate that a variety of different array formats are known and used in the art and can include a wide variety of different probe structures, substrate compositions and attachment technologies.

Expression profiles of genes within one or more of the gene signatures disclosed herein can be generated by employing reagents tailored for inclusion in the kits according to the present approach. Such reagents comprise a collection of gene specific nucleic acid primers and/or probes designed to selectively detect and/or amplify gene signature genes for use in detecting gene expression levels by using any assay format, e.g., polymerase-based assays (RT-PCR, TAQMAN™), hybridization-based assays, e.g., using DNA microarrays or other solid supports, nucleic acid sequence-based amplification assays, or flap endonuclease-based assays, or other nucleic acid quantification methods. Examples of gene specific primers and methods for their use can be found in U.S. Pat. No. 5,994,076, which is incorporated by reference in its entirety. The gene specific probe and/or primer collections may include only gene signature genes, or they may include probes and/or primers for additional genes. Accordingly, the probes and/or primers used in the kits embrace oligonucleotides or antisense nucleic acids that are wholly or partially complementary to the gene biomarkers from the gene signatures disclosed herein. In some embodiments, a kit of the present approach allows for the identification of candidates for mitochondrial inhibitor therapy, by a) analyzing a sample obtained from the patient for expression levels of the genes in at least one gene signature disclosed herein; and b) comparing the expression levels to control expression levels; c) identifying the patient as a candidate for mitochondrial inhibitor therapy based on the comparison.

The terminology used in the description of embodiments of the present approach is for the purpose of describing particular embodiments only and is not intended to be limiting. As used in the description and the appended claims, the singular forms "a," "an" and "the" are intended to include the plural forms as well, unless the context clearly indicates otherwise. The present approach encompasses numerous alternatives, modifications, and equivalents as will become apparent from consideration of the following detailed description.

It will be understood that although the terms "first," "second," "third," "a)," "b)," and "c)," etc. may be used herein to describe various elements of the present approach, and the claims should not be limited by these terms. These terms are only used to distinguish one element of the present approach from another. Thus, a first element discussed below could be termed an element aspect, and similarly, a third without departing from the teachings of the present approach. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the present approach described herein can be used in any combination. Moreover, the present approach also contemplates that in some embodiments, any feature or combination of features described with respect to demonstrative embodiments can be excluded or omitted.

As used herein, the transitional phrase "consisting essentially of" (and grammatical variants) is to be interpreted as encompassing the recited materials or steps "and those that do not materially affect the basic and novel characteristic(s)" of the claim. Thus, the term "consisting essentially of" as used herein should not be interpreted as equivalent to "comprising."

Having thus described certain embodiments of the present approach, it is to be understood that the scope of the appended claims is not to be limited by particular details set forth in the above description as many apparent variations thereof are possible without departing from the spirit or scope thereof as hereinafter claimed.

What is claimed is:

1. A method for reducing the likelihood of tumor metastasis and tumor recurrence in a patient, the method comprising:

obtaining a biological sample of a tumor from the patient;

determining, or having determined, the level of at least one mitochondrial biomarker in the biological sample of a cancer stem cell (CSC)-based mitochondrial-related gene signature selected from at least one of ACLY, VDAC3, HADH2, COX6B1, ATP5B, MCCC1, SLC25A10, TIMM8A, ECH1, ACACA, HSPA9, CHCHD2, and CCDC47;

comparing the determined level to a threshold level that is an expression level of a suitable non-tumor sample taken from the same individual or from a population for the at least one biomarker; and administering a pharmaceutically effective amount of at least one mitochondrial biogenesis inhibitor if the determined level exceeds the threshold level.

2. The method of claim 1, wherein the CSC-based mitochondrial-related gene signature is selected from the group consisting of ACLY, VDAC3, HADH2, COX6B1, ATP5B, MCCC1, SLC25A10, TIMM8A, ECH1, ACACA, HSPA9, CHCHD2, and CCDC47.

3. The method of claim 1, wherein the CSC-based mitochondrial-related gene signature is selected from a combination of ACLY, VDAC3, HADH2, and COX6B1.

4. The method of claim 1, wherein the at least one mitochondrial biogenesis inhibitor is selected from the group consisting of butane-1,4-bis-triphenyl-phosphonium, dodecyl-triphenyl-phosphonium, a)

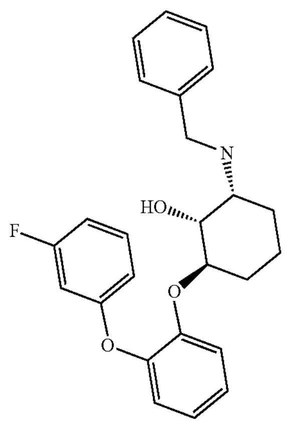

,

-continued b)

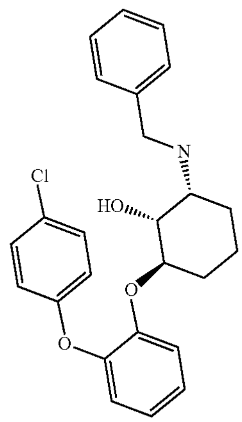

, c)

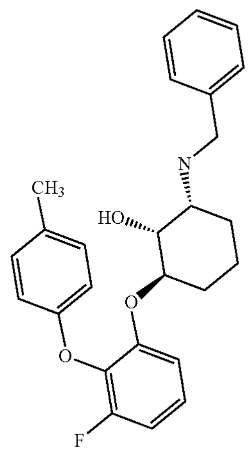

, d)

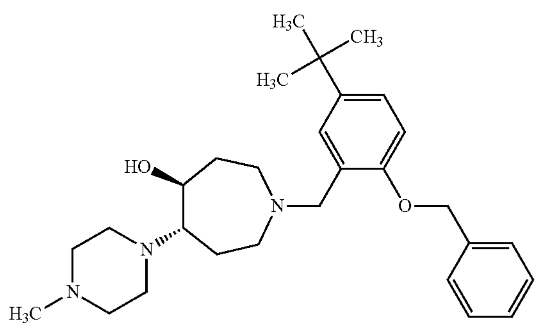

, e)

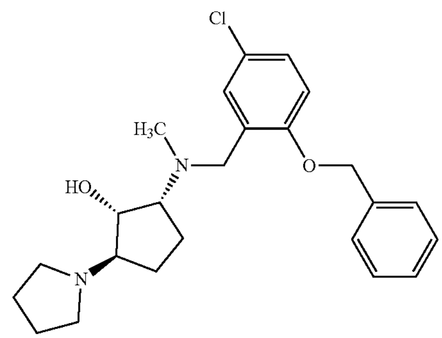

,

-continued f)

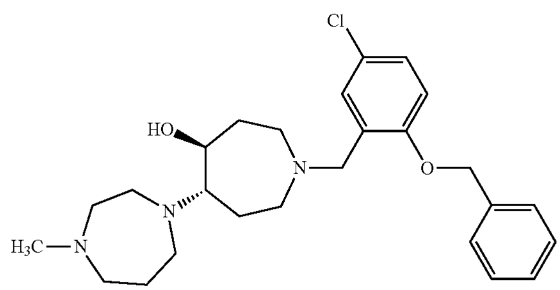

, g)

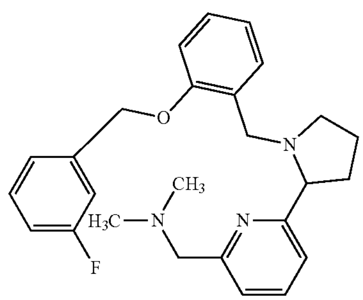

, h)

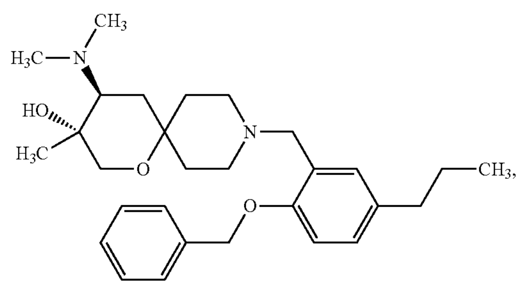

-continued i)

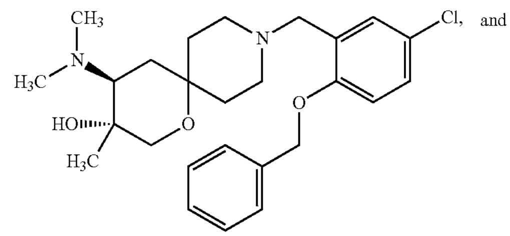

and

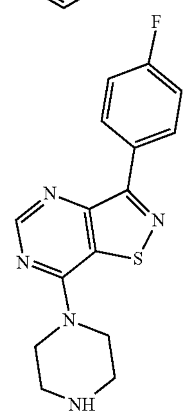

.

5. The method of claim 1, wherein the tumor comprises breast cancer.

6. The method of claim 1, wherein the mitochondrial biogenesis inhibitor is selected from the group consisting of tetracycline, doxycycline, tigecycline, minocycline, erythromycin, azithromycin, clarithromycin, pyrvinium pamoate, atovaquone, bedaquiline, irinotecan, sorafenib, niclosamide, berberine, stiripentol, chloroquine, etomoxir, perhexiline, a mitoriboscin, a mitoketoscin, a mitoflavoscin, a mitoflavin, a triphenyi-phosphonium (TPP)-moiety-containing derivative, an mitochondrial division inhibitor-1 (mDIVI1-1) moiety-containing derivative, caffeic acid phenyl ester, an antimitoscin, and a repurposcin.

* * * * *